United States Patent
Watanabe et al.

(10) Patent No.: US 7,332,622 B2
(45) Date of Patent: Feb. 19, 2008

(54) PROCESS FOR PREPARING OPTICALLY ACTIVE NITRO COMPOUNDS AND CYANO COMPOUNDS

(75) Inventors: Masahito Watanabe, Soka (JP); Kunihiko Murata, Koshigaya (JP); Takao Ikariya, Tokyo (JP)

(73) Assignee: Kanto Kaguku Kabushiki Kaisha, Chuo-ku, Tokyo (JP)

( * ) Notice: Subject to any disclaimer, the term of this patent is extended or adjusted under 35 U.S.C. 154(b) by 560 days.

(21) Appl. No.: 10/934,338

(22) Filed: Sep. 3, 2004

(65) Prior Publication Data

US 2005/0101787 A1   May 12, 2005

(30) Foreign Application Priority Data

Sep. 5, 2003  (JP) .............................. 2003-314096
Dec. 5, 2003  (JP) .............................. 2003-407981
Mar. 17, 2004 (JP) .............................. 2004-076663

(51) Int. Cl.
*C07C 255/00* (2006.01)
*C07C 69/76* (2006.01)

(52) U.S. Cl. ........................................ 558/368; 560/53
(58) Field of Classification Search ..................... None
See application file for complete search history.

(56) References Cited

U.S. PATENT DOCUMENTS 6,329,536 B1   12/2001   Ji et al.

FOREIGN PATENT DOCUMENTS

EP   1 308 435 A2   5/2003
WO   WO 00/15599   3/2000

OTHER PUBLICATIONS

Annamali, V. et al., "Catalysis of the Michael Addition Reaction by Late Transition Metal Complexes of BINOL-Derived Salens," J. Org. Chem. 68:1973-1981 (2003).

Brunner, H. et al., "Asymmetric Catalysis CIII [1]: Enantioselective Michael Addition of 1, 3-Dicarbonyl Compounds to Conjugated Nitroalkenes," Chem. Monthly 127:1063-1072 (1996).

Gomez-Bengoa, E. et al., "Michael Reaction of Stabilized Carbon Nucleophiles Catalyzed by [RuH$_2$(PPh$_3$)$_4$]," J. Am. Chem. Soc. 118:8553-8565 (1996).

Duursma, A. et al., "Highly Enantioselective Conjugate Addition of Dialkylzinc Reagents to Acyclic Nitroalkenes: A Catalytic Route to β$^2$-Amino Acids, Aldehydes, and Alcohols," J. Am. Chem. Soc. 125:3700(2003).

Haack, K. et al., "The Catalyst Precursor, Catalyst, and Intermediate in the Ru$^{II}$-13 Promoted Asymmetric Hydrogen Transfer between Alcohols and Ketones," Angew. Chem. Int. Ed. Engl. 36(3):285 (1997).

Hayashi, T. et al., "Rhodium-Catalyzed Asymmetric Conjugate Addition of Organoboronic Acids to Nitroalkenes," J. Am. Chem. Soc. 122:10716 (2000).

Ji, J. et al., "Catalytic Enantioselective Conjugate Addition of 1,3-Dicarbonyl Compounds to Nitroalkenes," J. Am. Chem. Soc. 121:10215 (1999).

Murata, K. et al., "New Chiral Rhodium and Iridium Complexes with Chiral Diamine Ligands for Asymmetric Transfer Hydrogenation of Aromatic Ketones," J. Org. Chem. 64:2186 (1999).

Sewald, N. et al., "Enantioselective Copper(I) Catalyzed 1,4-Addition of Diethylzinc to Nitroolefins," Tetrahedron:Asymmetry 9:1341 (1998).

Watanabe, M. et al., "Enantioselective Michael Reaction Catalyzed by Well-Defined Chiral Ru Amido Complexes: Isolation and Characterization of the Catlyst Intermediate, Ru Malonato Complex Having a Metal—Carbon Bond," J. Am. Chem. Soc. 125:7508 (2003).

*Primary Examiner*—Paul A. Zucker
(74) *Attorney, Agent, or Firm*—Wolf, Greenfeild & Sacks, P.C.

(57) ABSTRACT

A process for preparing optically active nitro compounds and cyano compounds using a metal complex, which is obtained by reaction of an optically active nitrogen-containing compound and a periodic table group VIII metal complex, in the asymmetric Michael reaction.

8 Claims, No Drawings

PROCESS FOR PREPARING OPTICALLY ACTIVE NITRO COMPOUNDS AND CYANO COMPOUNDS

FIELD OF THE INVENTION

The invention relates to a process for preparing a nitro compound and a cyano compound in high efficiency and high stereoselectivity using a transition metal complex, which makes an optically active nitrogen-containing compound an asymmetric ligand, as a catalyst for an asymmetric Michael reaction.

BACKGROUND OF THE INVENTION

Among optically active compounds there are a lot of very useful compounds as intermediates of drugs, etc. In particular, nitrogen-containing compounds such as optically active nitro compounds or optically active cyano compounds are especially interesting due to wide application fields as synthetic intermediates for drug Rolipram, GABAB receptor agonist Baclofen, immune drug β-methyl carbapenem and the like, and as building blocks for endothlin A antagonist ABT-546 and the like.

Various methods have been developed as synthetic methods for optically active nitro compounds, wherein as to an asymmetric Michael reaction using an asymmetric metal catalyst, reaction making the rhodium complex its catalyst has been reported (J. Am. Chem. Soc. 2000, 122, 10716). Reactions making asymmetric copper complexes as catalysts have also been reported (Tetrahedron Asymmetry 1998, 9, 1341 and J. Am. Chem. Soc. 2003, 125, 3700). Further, reactions making asymmetric magnesium complexes as catalysts have been reported (International publication 00/15599 Pamphlet, U.S. Pat. No. 6,329,536 and J. Am. Chem. Soc. 1999, 121, 10215).

However, since in the method discussed in J. Am. Chem. Soc. 2000, 122, 10716, alkylboronic acid is used as a nucleophile, it is necessary to prepare the alkylboronic acid in advance, and in the reaction there are tedious problems that it is necessary to add the prepared alkylboronic acid in an more amount than an electrophile and further to react in a relatively high temperature, etc. Also, in the methods described in Tetrahedron Asymmetry 1998, 9, 1341 and J. Am. Chem. Soc. 2003, 125, 3700, dialkylzinc unstable in the air is used as a reagent and it is necessary to keep the reaction temperature from −30° C. to −78° C. in order to obtain a relatively high enantioselectivity. Further, in the methods in International publication 00/15599 Pamphlet and U.S. Pat. No. 6,329,536 and in J. Am. Chem. Soc. 1999, 121, 10215, reactions of dicarbonyl compounds with nitroalkenes are investigated, though in order to get Michael adducts in high yield and high selectivity it is necessary to add a relatively high amount of catalyst in about 5 mol % and further to add molecular sieve and an amine as promoter. Based on this, although a magnesium complex alone act as Lewis acid and activates the dicarbonyl compounds, it has no function to fully accelerate deprotonation of the dicarbonyl compounds and is not necessarily an effective catalyst system.

Accordingly, the methods to synthesize these optically active nitro compounds have not necessarily been high in utility because of use of unstable reagents, use of a large catalyst amount, further, necessity of a high temperature or low temperature reaction conditions, and a long time reaction and the like.

Further, as to an optically active cyano compound, of course it itself and also an optically active amine compound obtained by reduction of the cyano group of said compound are extremely important compounds as building blocks for drugs, etc., though its rational synthetic method has not been fully developed yet, and the synthetic method of the optically active cyano compound by Michael reaction has not been known yet.

In the mean time, although reactions to add malonic acid diesters to substrates stereoselectively using a ruthenium catalyst which makes a chiral diamine as ligand have been reported (J. Am. Chem. Soc. 2003, 125, 7508), compounds as a Michael acceptor are only disclosed for cyclic enones such as cyclopentenone, cyclohexenone and cycloheptenone, and therefore, in the reactions only optically active carbonyl compounds are obtained.

Consequently, further development of a rational synthetic method of optically active nitro or cyano compounds, which are interesting for manufacturing drugs, etc., is seriously needed.

SUMMARY OF THE INVENTION

In one aspect, the invention addresses the problems outlined above and provides for the preparation of nitro compounds and cyano compounds in high efficiency and high stereoselectivity.

The inventors extensively investigated application of various asymmetric catalysts consisting of a chiral ligand and a metal complex to an asymmetric Michael reaction and have found that nitro compounds and cyano compounds could be obtained in high efficiency and high stereoselectivity using a metal complex, which was obtained by reaction of an optically active nitrogen-containing compound and a periodic table group VIII metal complex, in the asymmetric Michael reaction, and accomplished this aspect of the invention.

Namely, the invention relates to a process for preparing an optically active compound, wherein a compound represented by the general formula (A)

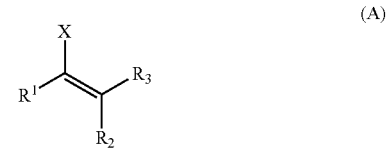

(A)

(wherein $R^1$ is an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s), or is a hydrogen atom, a halogen atom, a carboxyl, ester, amido, hydroxyl, alkoxy or amino group. $R^2$ and $R^3$ are each independently a hydrogen atom, an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s). X is a nitro or cyano group. Also, $R^2$ and $R^3$ can be different groups, and further $R^1$ and $R^2$, $R^1$ and $R^3$ or $R^2$ and $R^3$ can form a ring binding each other.) and a compound represented by the general formula (B)

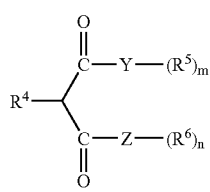
(B)

(wherein R[4] is a hydrogen atom, a halogen atom, a amido, amino, alkoxy, nitro or cyano group, an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s), R[5] and R[6] are each independently a hydrogen atom, an aromatic monocyclic or aromatic polycyclic hydrocarbon group which can have (a) substituent(s), a saturated or unsaturated aliphatic or alicyclic hydrocarbon group which can have (a) substituent(s), or a straight or branched alkoxyl group of carbon number 1 to 20. Also, R[4] and R[5], R[4] and R[6], or R[5] and R[6] can form a ring binding each other. Y and Z represent each other independently a single bond, an oxygen, sulfur, nitrogen or phosphorus atom, and m and n are each other independently 1 or 2. In the case that Y and Z are a single bond, an oxygen or sulfur atoms, m and n are 1, and in the case that Y and Z are a nitrogen or phosphorus atom, m and n are 2.) are reacted with an asymmetric metal complex obtained by the action of an optically active nitrogen-containing compound and a periodic table group VIII metal complex, affording said optically active compounds represented by the general formula (C)

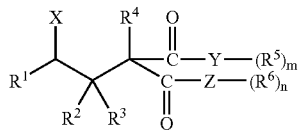
(C)

(wherein R[1], R[2], R[3], R[4], R[5], R[6], X, Y, Z, m and n have the same meaning as described above.).

Also, the invention relates to the process for preparing the above optically active compound, wherein Y and Z in above compound (B) are both oxygen atoms.

Further, the invention relates to the process for preparing above optically active compound, wherein Y in above compound (B) is an oxygen atom and Z is a single bond, or Y is a single bond and Z is an oxygen atom.

Also, the invention relates to the process for preparing the above optically active compound, wherein the structure of an optically active nitrogen-containing compound is represented by the general formula (D)

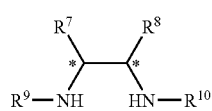
(D)

(wherein R[7] and R[8] are each independently an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s). Also, R[7] and R[8] can form a ring binding each other. R[9] and R[10] are each independently a hydrogen atom, an alkyl, acyl, carbamoyl, thioacyl, thiocarbamoyl, alkylsulfonyl or arylsulfonyl group. * represents an asymmetric carbon atom.).

Further, the invention relates to the process for preparing the above optically compound, wherein in an optically active nitrogen-containing compound represented by the general formula (D), R[10] is represented by the structure

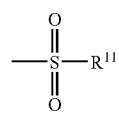

(wherein R[11] is an alkyl or aryl group which can have (a) substituent(s).).

Also, the invention relates to the process for preparing the above optically active compound, wherein in the optically active nitrogen-containing compound represented by the general formula (D), R[7] is represented by the structure,

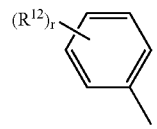

R[8] is represented by the structure,

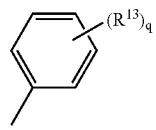

and R[10] is represented by the structure

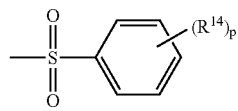

(wherein R[12], R[13] and R[14] are each independently a hydrogen atom, an alkyl group, a halogen atom or an alkoxyl group. p, q and r are each independently an integer of 1 to 5.).

Further, the invention relates to the process for preparing the above optically active compound, wherein the periodic table group VIII metal complex is a ruthenium compound.

Also, the invention relates to the process for preparing the above optically active compound, wherein the asymmetric metal complex is a asymmetric ruthenium amido complex represented by the general structure (E)

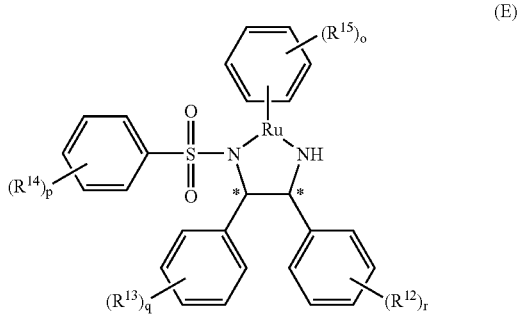

(wherein $R^{12}$, $R^{13}$, $R^{14}$, p, q and r have the same meaning as described above, $R^{15}$ is a methyl, ethyl, propyl, isopropyl or tert-butyl group, and o is an integer of 0 to 6. * represents an asymmetric carbon atom.).

Further, the invention relates to the process for preparing the above optically active compound, wherein the asymmetric metal complex is an asymmetric ruthenium hydrido complex represented by the general structure (F)

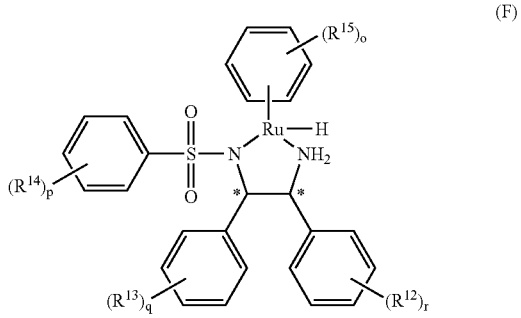

(wherein $R^{12}$, $R^{13}$, $R^{14}$, $R^{15}$, o, p, q and r have the same meaning as described above. * represents an asymmetric carbon atom.).

According to the invention, it is possible to obtain Michael adducts such as an optically active nitro compound and an optically active cyano compound in a high efficiency and a high stereoselectivity by a simple procedure. This can greatly contribute to the synthesis of drugs, in particular, such as Rolipram.

In the meantime, generally, in the field of organic chemistry, if an electron-attracting group of Michael acceptor is different, the electronic state of a whole molecule becomes totally different, and therefore even the same asymmetric catalyst is different in its catalytic action depending on a type of the electron-attracting group of Michael acceptor. For example, since nitroalkenes have a strong electron-attracting nitro group, it is known that an anionic polymerization occurs easily under the presence of a base. Therefore, because a ruthenium catalyst which makes a chiral diamine as ligand is a basic catalyst, it was not clear whether said catalyst could be applied in the asymmetric Michael reaction between the nitroalkene and malonic acid diester.

In spite of the above general information, by using an asymmetric catalyst, which is obtained by reaction of a particular optically active nitroger-containing compound with a periodic table group VIII metal complex, in the Michael reaction of a nitroalkene or a cyanoalkene with a 1,3-dicarbonyl compound, the invention makes it possible to prepare an optically active nitro compound and an optically active cyano compound which are extremely useful for the synthesis of various medicinal compounds, etc. under room temperature, a short time, small amount of catalyst, a simple procedure, and moreover in high efficiency and high stereoselectivity, greatly contributing to said technical field.

DETAILED DESCRIPTION

The function and advantage of these and other embodiments of the present invention will be more fully understood from the examples below. The following examples are intended to illustrate the benefits of the present invention, but do not exemplify the full scope of the invention.

A compound used as a starting material in the invention is represented by the above general formula (A).

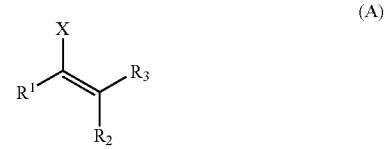

(wherein $R^1$ is an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s), or is a hydrogen atom, a halogen atom, a carboxyl, ester, amido, hydroxyl, alkoxyl or amino group. $R^2$ and $R^3$ are each independently a hydrogen atom, an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s). X is a nitro or cyano group. Also, $R^2$ and $R^3$ can be different groups, and further, $R^1$ and $R^2$, $R^1$ and $R^3$ or $R^2$ and $R^3$ can form a ring binding each other.).

By a combination which makes $R^2$ and $R^3$ different can be prepared an optically active compound in which a-position of the X group is an asymmetric carbon.

Specific examples of the aromatic monocyclic or aromatic polycyclic hydrocarbon group include phenyl, 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-tert-butylphenyl, 4-vinylphenyl, cumenyl, mesityl, xylyl, 1-naphthyl, 2-naphthyl, anthryl, phenanthryl and indenyl groups, etc.

The aliphatic hydrocarbon group is a straight chain or branched alkyl, alkenyl or alkynyl group which can be each substituted by an aromatic hydrocarbon or aromatic heteroring groups. With regard to examples of the alkyl group, there can be cited alkyl groups of carbon number 1 to 20 such as methyl, ethyl, n-propyl, isopropyl, butyl, secbutyl, tert-butyl, pentyl, isopentyl, neopentyl, tert-pentyl, hexyl, heptyl, octyl, nonyl, decyl and dodecyl groups. With regard to examples of the alkenyl group, there can be cited alkenyl groups of carbon number 2 to 20 such as vinyl, 1-propenyl, 2-propenyl, 1-butenyl, 1-isopropenyl, 2-butenyl, 3-butenyl, 1,3-butadienyl, 1-pentenyl, 2-pentenyl and 3-pentenyl groups. With regard to examples of the alkynyl group, there can be cited alkynyl groups of carbon number 2 to 20 such as ethynyl, propynyl and phenylethynyl group. The alicyclic hydrocarbon group is cycloalkyl group which can be each substituted by am aromatic hydrocarbon or aromatic hetero-ring group. With regard to examples of cycloalkyl group, there can be cited are cycloalkyl groups of carbon number 3 to 8 such as cyclopropyl, cyclobutyl, cyclopentyl and cyclohexyl groups.

With regard to examples of the hetero-monocyclic or hetero-polycyclic group, there can be cited thienyl, furyl, pyranyl, pyrrolyl, imidazolyl, pyrazolyl, oxazolyl, isooxazolyl, triazolyl, thiazolyl, isothiazolyl, pyridyl, pyridazinyl, pyrazinyl, benzoimidazolyl, benzopyrazolyl, benzothiazolyl, quinolyl, anthranyl, indolyl, and phenanthrolinyl group.

As the substituents bound to these aromatic hydrocarbon group, aromatic hetero-ring group, aliphatic hydrocarbon group or alicyclic hydrocarbon group, illustrative are specifically halogen atoms such as fluorine, chlorine, bromine and iodine, halogen-containing hydrocarbon groups such as trifluoromethyl group, oxygen-containing substituents such as hydroxyl, alkoxyacyl, alkoxycarbonyl and carboxyl group, nitrogen-containing substituents such as amino, alkylamino, nitro, cyano and azido group, silicon-containing substituents such as trimethylsilyl and hydrosilyl group, sulfur-containing substituents such as mercapto and alkylthio group, phosphorus-containing substituents such as phosphoryl and triphenylphosphinyl group, etc. As transition metal-containing substituents, illustrative are specifically iron-containing substituents such as a ferrocenyl group. Also, $R^1$ and $R^2$, $R^1$ and $R^3$ or $R^2$ and $R^3$ can form a ring binding each other. As specific examples of the compounds represented by the general formula (A) are illustrated the compounds shown in the compound group-1, and those particularly high in applicability are trans-β-nitrostylene (compound group 1-1), 4-chloro-β-nitrostylene (compound group 1-4), 4-methyl-β-nitrostylene (compound group 1-2) and cinnamonitrile (compound group 1-26). Further, the compounds represented by the general formula (A) are not limited to the compounds in the compound group-1.

Compound group-1

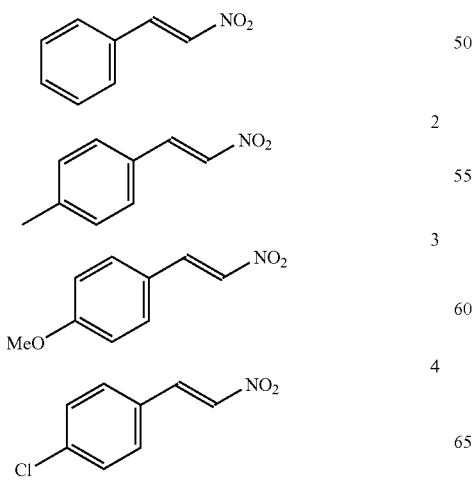

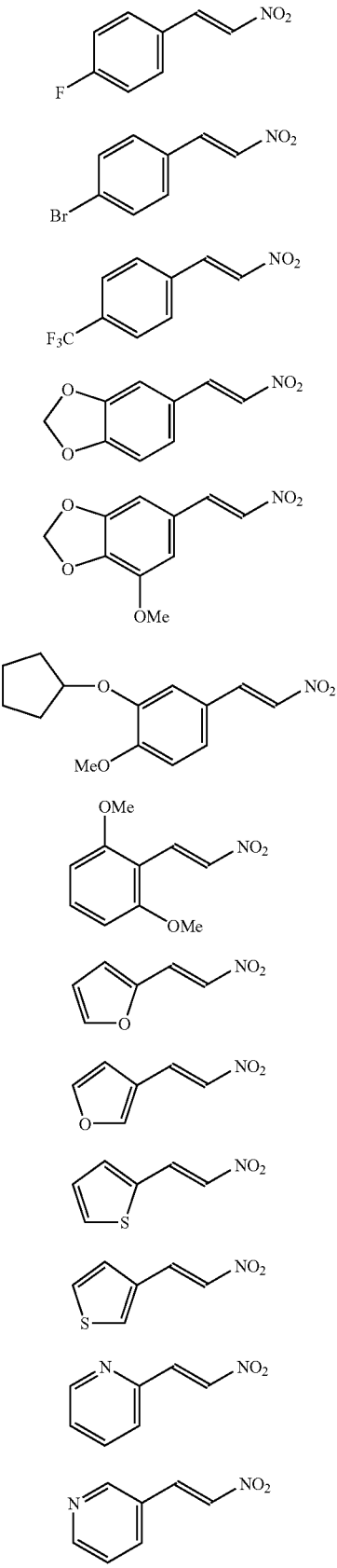

-continued
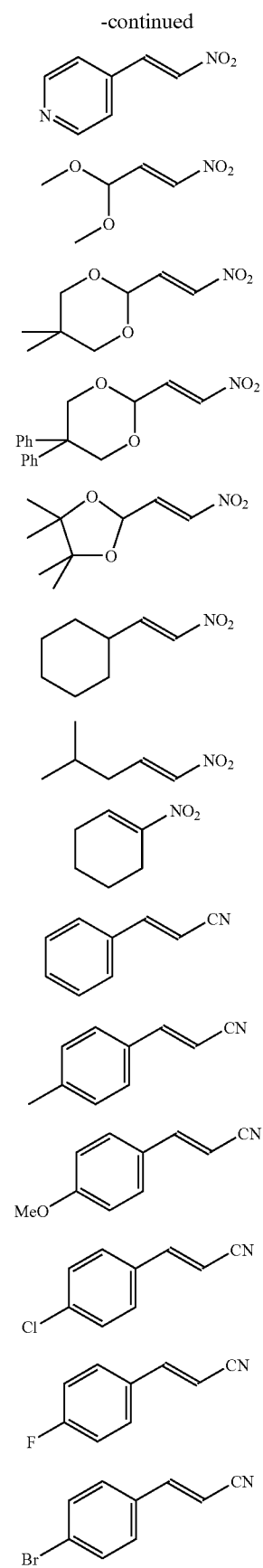
-continued
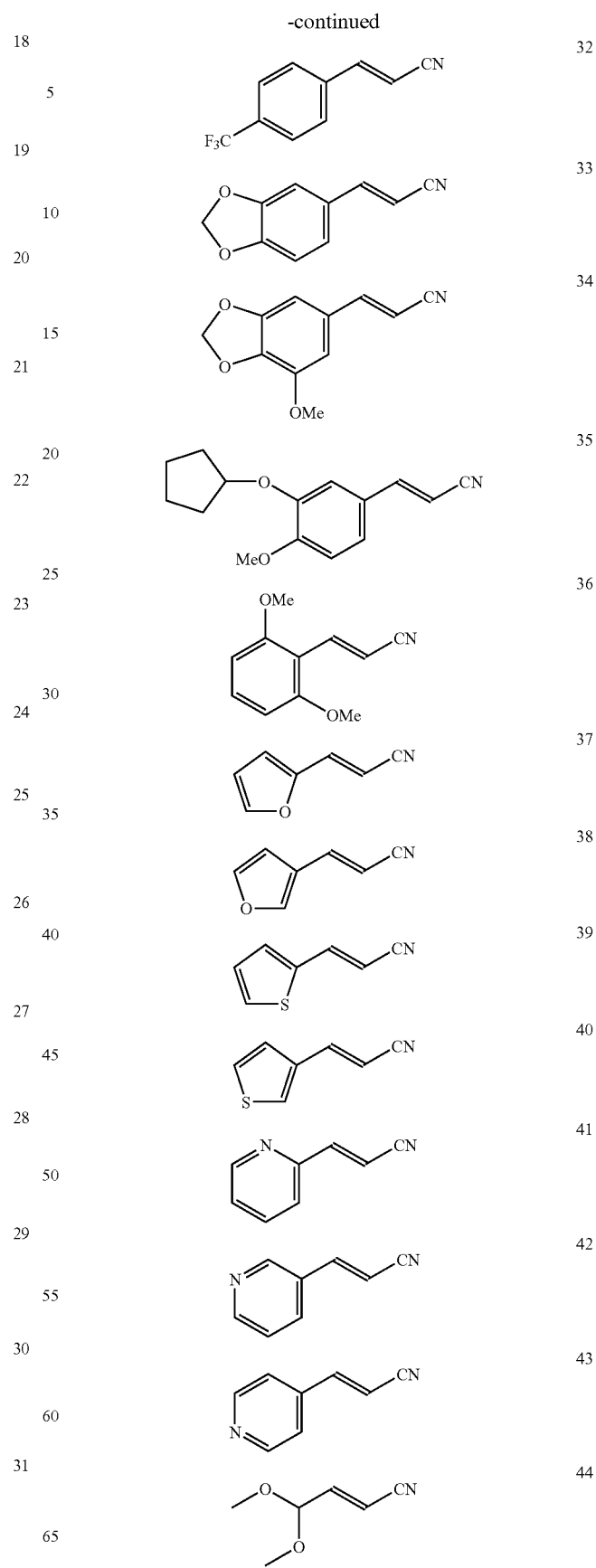

-continued

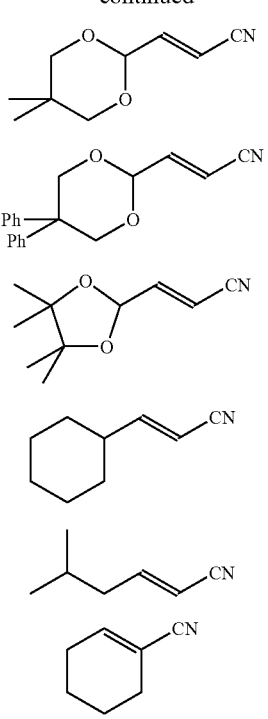

The amount of a compound represented by the general formula (A) is usually shown by the molar ratio (S/C) of a reaction substrate against an asymmetric metal catalyst having a periodic table group VIII metal atom, S/C being 10-100,000, preferably 50-2,000.

The compounds, which are a Michael donor of a starting material in the invention, are represented by the general formula (B).

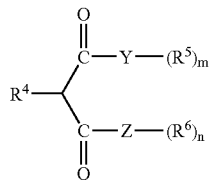

(B)

In the general formula (B), $R^4$ is a hydrogen atom, a halogen atom, an amido, amino, alkoxyl, nitro or cyano groups, an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s), $R^5$ and $R^6$ are each independently a hydrogen atom, an aromatic monocyclic or aromatic polycyclic hydrocarbon group which can have (a) substituent(s), a saturated or unsaturated aliphatic or alicyclic hydrocarbon group which can have (a) substituent(s), or a straight or branched alkoxyl groups of carbon number 1 to 20. Also, $R^4$ and $R^5$, $R^4$ and $R^6$, or $R^5$ and $R^6$ can form a ring binding each other. Y and Z represent each other independently a single bond, a oxygen, sulfur, nitrogen or phosphorus atom, and m and n are each other independently 1 or 2. In the case that Y is a single bond, m is 1, and in the case that Z is a single bond, n is 1. In the case that Y is an oxygen or sulfur atom, m is 1, and in the case that it is a nitrogen or phosphorus atom, m is 2. In the case that Z is an oxygen or sulfur atom, n is 1, and in the case that it is a nitrogen or phosphorus atom, n is 2.

In the general formula (B), $R^4$, $R^5$ and $R^6$ are each independent, though each term has the above meaning in the definition of each group.

Halogen atoms are fluorine, chlorine and bromine atom and the like, and alkoxy groups are alkoxy groups of carbon number 1 to 10, for example, including methoxy, ethoxy, propoxy and isopropoxy group.

As specific examples of the compounds represented by the general formula (B) are illustrated the compounds shown in FIG. 2, and those particularly high in applicability are dimethyl malonate (compound group-2-1), diethyl malonate (compound group-2-2), and methyl acetoacetate (compound group-2-10). Further, the compounds represented by the general formula (B) are not limited to the compounds in the compound group-2, and it is possible to make the carbon, at which a bond is newly formed, an asymmetric carbon by a different combination of —Y—$(R^5)$m and -Z-$(R^6)$n in the general formula (B) (for example, 8 to 23 in compound group-2).

Compound group-2

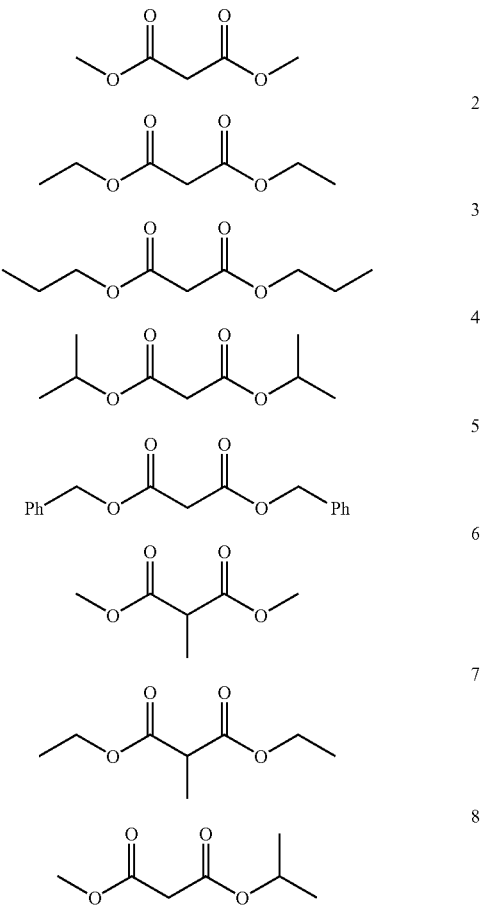

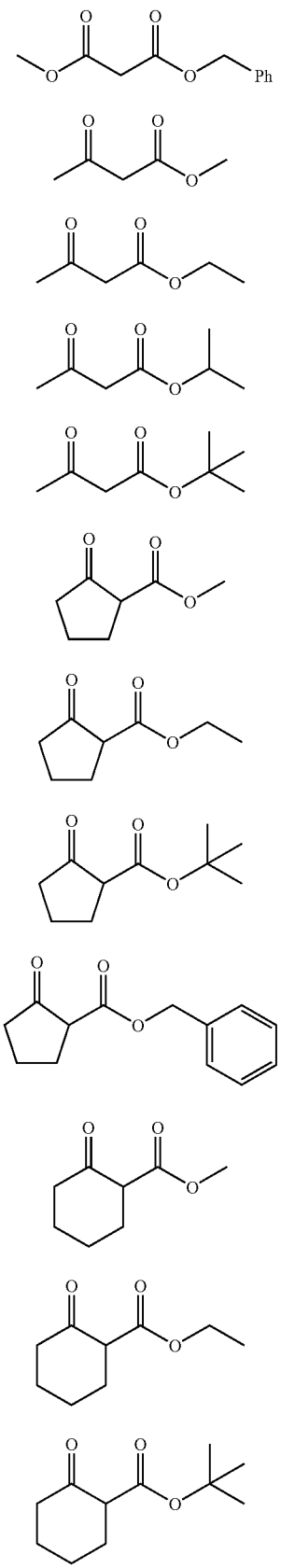

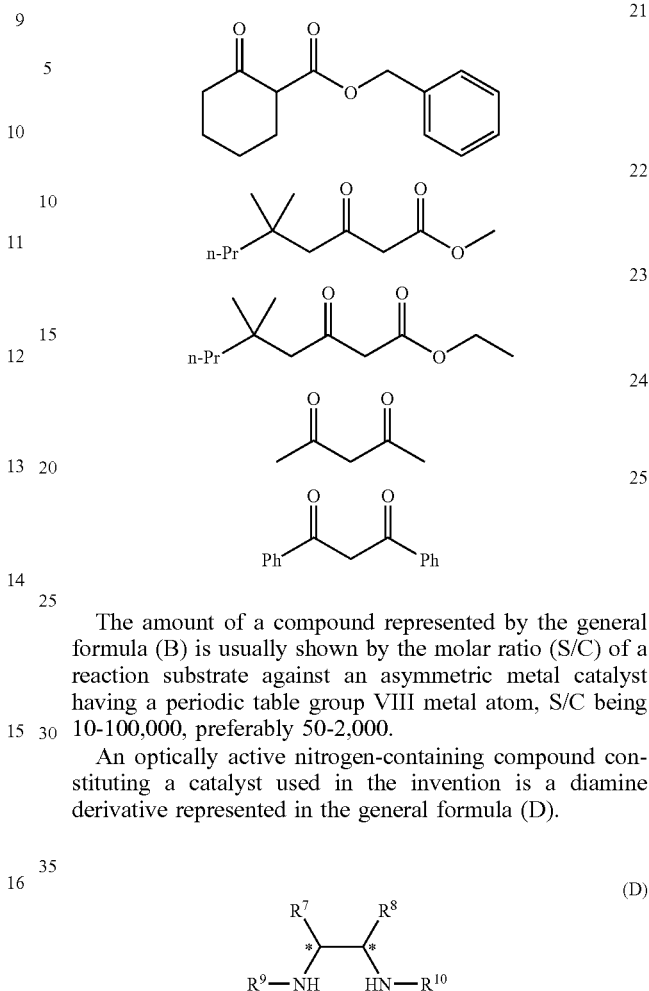

The amount of a compound represented by the general formula (B) is usually shown by the molar ratio (S/C) of a reaction substrate against an asymmetric metal catalyst having a periodic table group VIII metal atom, S/C being 10-100,000, preferably 50-2,000.

An optically active nitrogen-containing compound constituting a catalyst used in the invention is a diamine derivative represented in the general formula (D).

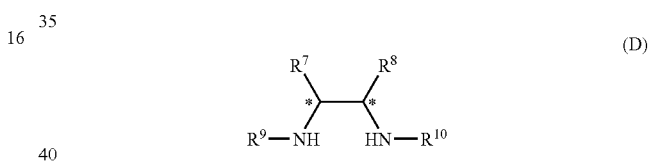

In the general formula (D), $R^7$ and $R^8$ are alkyl groups, for example, including a straight chain or branched chain alkyl groups of carbon number 1 to 6 such as methyl, ethyl, n-propyl, isopropyl, butyl, sec-butyl, tert-butyl, pentyl, isopentyl, neopentyl, tert-pentyl and hexyl, aryl groups such as phenyl, naphthyl, 4-methylphenyl, 3,5-dimethylphenyl and 4-methoxyphenyl, aromatic hetero-ring groups such as furyl and pyridyl. Further, $R^7$ and $R^8$ together can be tetraethylene group (forming cycohexane ring). These groups can also be substituted, and the substituents are one or more groups selected from lower alkyl groups such as methyl, ethyl, n-propyl and isopropyl, lower alkoxy group such as methoxy and ethoxy group, and halogen atoms such as chlorine, bromine and fluorine atoms. As $R^7$ and $R^8$, phenyl and substituted phenyl group, and the like are preferable.

$R^9$ and $R^{10}$ are a hydrogen atom; lower alkyl groups, for example, a straight chain or branched chain alkyl groups of carbon number 1 to 6 such as methyl, ethyl, n-propyl and isopropyl; acyl groups, for example, such as acetyl, propionyl and bezoyl; carbamoyl groups, for example, such as N-methyl carbamoyl and N-phenylcarbamoyl; thioacyl groups, for example, such as thioacetyl, thiopropionyl and thiobezoyl; thiocarbamoyl groups, for example, such as N-methylthiocarbamoyl and N-phenylthiocarbamoyl; alkylsulfonyl or arylsulfonyl groups, for example, alkylsulfonyl or arylsulfonyl groups of carbon number 1 to 20 such as methanesulfonyl, ethanesulfonyl, trifluoromethanesulfonyl, benzenesulfonyl, 2,4,6-trimethyl-benzenesulfonyl, 2,4,6-triisopropylbenzenesulfonyl, pentamethylbenzenesulfonyl, 4-tert-butylbenzenesulfonyl, 4-methoxybenzenesulfonyl, 4-chlorobenzenesulfonyl and p-toluenesulfonyl group. As to $R^9$ and $R^{10}$, at least one group is preferably a hydrogen atom. More preferably, as $R^9$ and $R^{10}$, one group is an arylsulfonyl group, with 2,4,6-triisopropylbenzenesulfonyl and pentamethylbenzenesulfonyl being particularly preferable.

In the optically active nitrogen-containing compounds represented by the general formula (D), diamine derivatives are preferable, wherein $R^{10}$ is represented by

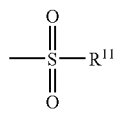

(wherein $R^{11}$ is an alkyl or aryl group which can have (a) substituent(s).), and $R^7$,

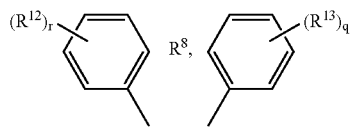

and $R^{10}$ is represented by

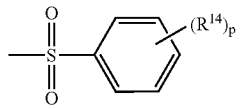

(wherein $R^{12}$, $R^{13}$ and $R^{14}$ are each independently a hydrogen atom, a lower alkyl group, a halogen atom or a lower alkoxy group. p, q and r are each independently an integer of 1 to 5.). As specific diamine derivatives, illustrative are, for example, 1,2-diphenylethylenediamine, N-methyl-1,2-diphenylethylenediamine, N-(p-toluenesulfonyl)-1,2-diphenylethylenediamine, N-methanesulfonyl-1,2-diphenylethylenediamine, N-methyl-N'-(p-toluenesulfonyl)-1,2-diphenylethylenediamine, N-(p-methoxyphenylsulfonyl)-1,2-diphenylethylenediamine, N-(p-chlorophenylsulfonyl)-1,2-diphenylethylenediamine, N-trifluoromethanesulfonyl-1,2-diphenylethylenediamine, N-(2,4,6-trimethylbenzenesulfonyl)-1,2-diphenylethylenediamine, N-(2,4,6-triisopropylbenzenesulfonyl)-1,2-diphenylethylenediamine, N-(4-tert-butylbenzenesulfonyl)-1,2-diphenylethylenediamine, N-(2-naphthylsulfonyl)-1,2-diphenylethylenediamine, N-(3,5-dimethylbenzenesulfonyl)-1,2-diphenylethylenediamine, N-pentamethylbenzenesulfonyl-1,2-diphenylethylenediamine, etc.

The amount of the optically active nitrogen-containing compound against a starting material is usually used in 1-1,000,000, preferably 5-5,000 by the molar ratio (S/C) of the optically active nitrogen-containing compound against the starting material.

As a metal species of a periodic table group VIII metal compound used in combination with these asymmetric ligands, illustrative are ruthenium, rhodium, iridium, cobalt, iron, nickel, palladium, platinum and osmium, with ruthenium being particularly preferable. Specific compounds includes $RuCl_3\text{-}3H_2O$, $[RuCl_2(\text{p-cymene})]_2$, $[RuCl_2(\text{benzene})]_2$, $[RuCl_2(\text{mesitylene})]_2$, $[RuCl_2(1,2,4,5\text{-tetramethylbenzene})]_2$, $[RuCl_2(\text{pentamethylbenzene})]_2$, $[RuCl_2(\text{hexamethylbenzene})]_2$, $RuCl_2(PPh_3)_3$, $[RuCl_2(\text{cod})]_2$, $[RuCl_2(CO)_3]_2$, $[Rh(\text{cod})Cl]_2$, $[RhCl_2(\text{pentamethylcycloheptadienyl})]_2$, $[IR(\text{cod})Cl]_2$, $CoCl_2$, $NiCl_2$, $NiBr_2$, $NiCl_2(PPh_3)_2$, $NiBr_2(PPh_3)_2$, $PdCl_2$, $Pd(PPh_3)_4$, $PdCl_2(CH_3CN)_2$, $PdCl_2(PhCN)_2$, $PtCl_2(\text{cod})$, $Pt(PPh_3)_4$, $RuH_2(PPh_3)_4$, $RuH_2(\text{dppe})_2$, $RuH_4(PPh_3)_3$, $Ru(\text{cod})(\text{cot})$, $Ru(\text{cod})(\text{benzene})$, etc., preferably $[RuCl_2(\text{p-cymene})]_2$, $[RuCl_2(\text{mesitylene})]_2$, $[RuCl_2(1,2,4,5\text{-tetramethylbenzene})]_2$, $[RuCl_2(\text{pentamethylbenzene})]_2$, $[RuCl_2(\text{hexamethylbenzene})]_2$, $RuH_2(PPh_3)_4$, $RuH_2(\text{dppe})_2$, $RuH_4(PPh_3)_3$, $Ru(\text{cod})(\text{cot})$ and $Ru(\text{cod})(\text{benzene})$. Further, in the above compounds Ph is phenyl group, cod is cyclooctadiene, and cot is cyclooctatetraene.

The amount of the periodic table group VIII metal compound against a starting material is usually 10-100,000, preferably 50-500 in the molar ratio (S/C) of the periodic table group VIII metal compound against the starting material.

The mix ratio the periodic table group VIII metal compound to the optically active nitrogen-containing compound is 1.0:0.1 to 1.0:10.0 in molar ratio, preferably equivalent mole.

Although the asymmetric metal complex, in which the optically active nitrogen-containing compound is coordinated to the periodic table group VIII metal compound used as a catalyst, is obtained by reaction of the periodic table group VIII metal compound and the optically active nitrogen-containing compound, here a base can be used, and as the base used, illustrative are alkaline metal hydroxides such as lithium hydroxide, sodium hydroxide and potassium hydroxide, alkaline metal alkoxides such as lithium methoxide, sodium methoxide, sodium ethoxide and potassium isopropoxide, and organic amines such as trimethylamine, triethylamine and triisopropylamine.

Also, as a complex, in which the optically active nitrogen-containing compound is coordinated to the periodic table group VIII metal compound used as a catalyst, an amido complex represented by the general formula (E) and a hydrido complex represented by the general formula (F) can be illustrated.

In the general formula (E),

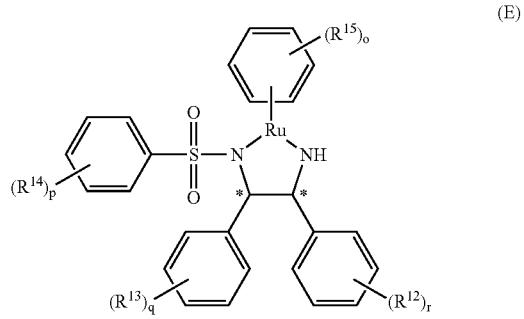

wherein $R^{12}$, $R^{13}$, $R^{14}$, p, q and r have the same meaning as described above, $R^{15}$ is a methyl, ethyl, propyl, isopropyl or tert-butyl group, and o is an integer of 0 to 6. * represents an asymmetric carbon atom.

In the general formula (F),

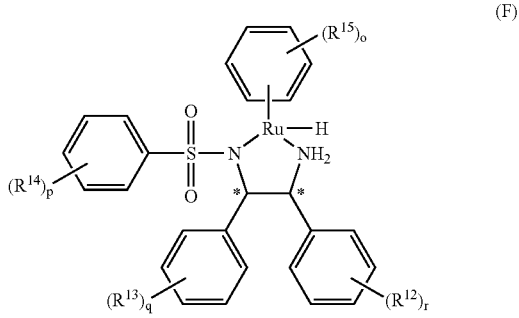

wherein $R^{12}$, $R^{13}$, $R^{14}$, $R^{15}$, o, p, q and r have the same meaning as described above. * represents an asymmetric carbon atom.

As specific examples of the ruthenium amido complexes represented by the general formula (E), illustrative are
[(S,S)-N-(p-toluenesulfonyl)-1,2-diphenylethylenediamine]-benzeneruthenium,
[(R,R)-N-(p-toluenesulfonyl)-1,2-diphenylethylenediamine]benzeneruthenium,
[(S,S)-N-(p-toluenesulfonyl)-1,2-diphenylethylenediamine](p-cymene)ruthenium,
[(R,R)-N-(p-toluenesulfonyl)-1,2-diphenylethylenediamine](p-cymene)ruthenium,
[(S,S)-N-(p-toluenesulfonyl)-1,2-diphenylethylenediamine](mesitylene)-ruthenium,
[(R,R)-N-(p-toluenesulfonyl)-1,2-diphenylethylenediamine]-(mesitylene)ruthenium,
[(S,S)-N-(p-toluenesulfonyl)-1,2-diphenylethylenediamine](1,2,4-trimethylbenzene)ruthenium,
[(R,R)-N-(p-toluenesulfonyl)-1,2-diphenylethylenediamine](1,2,4-trimethylbenzene)-ruthenium,
[(S,S)-N-(p-toluenesulfonyl)-1,2-diphenyl-ethylenediamine](1,2,4,5-tetramethylbenzene)ruthenium,
[(R,R)-N-(p-toluenesulfonyl)-1,2-diphenylethylene-diamine](1,2,4,5-tetramethylbenzene)ruthenium,
[(S,S)-N-(p-toluenesulfonyl)-1,2-diphenylethylenediamine](1,2,3,4-tetramethylbenzene)ruthenium,
[(R,R)-N-(p-toluenesulfonyl)-1,2-diphenylethylenediamine](1,2,3,4-tetramethylbenzene)-ruthenium,
[(S,S)-N-(p-toluenesulfonyl)-1,2-diphenylethylenediamine](pentamethylbenzene)ruthenium,
[(R,R)-N-(p-toluenesulfonyl)-1,2-diphenylethylenediamine]-(pentamethylbenzene)ruthenium,
[(S,S)-N-(p-toluenesulfonyl)-1,2-diphenylethylenediamine](hexamethylbenzene)ruthenium,
[(R,R)-N-(p-toluenesulfonyl)-1,2-diphenylethylenediamine]-(hexamethylbenzene)ruthenium,
[(S,S)-N-methanesulfonyl-1,2-diphenylethylenediamine]benzeneruthenium,
[R,R)-N-methanesulfonyl-1,2-diphenylethylenediamine]benzeneruthenium,
[(S,S)-N-methanesulfonyl-1,2-diphenylethylenediamine](p-cymene)ruthenium,
[(R,R)-N-methanesulfonyl-1,2-diphenylethylenediamine](p-cymene)ruthenium,
[(S,S)-N-methanesulfonyl-1,2-diphenylethylenediamine]-(mesitylene)ruthenium,
[(R,R)-N-methanesulfonyl-1,2-diphenylethylenediamine](mesitylene)ruthenium,
[(S,S)-N-methanesulfonyl-1,2-diphenylethylenediamine](1,2,4-trimethylbenzene)ruthenium,
[(R,R)-N-methanesulfonyl-1,2-diphenylethylenediamine](1,2,4-trimethylbenzene)ruthenium,
[(S,S)-N-methanesulfonyl-1,2-diphenylethylenediamine]-(1,2,4,5-tetramethylbenzene)ruthenium,
[(R,R)-N-methanesulfonyl-1,2-diphenylethylenediamine](1,2,4,5-tetramethylbenzene)ruthenium,
[(S,S)-N-methanesulfonyl-1,2-diphenylethylenediamine](1,2,3,4-tetramethylbenzene)-ruthenium,
[(R,R)-N-methanesulfonyl-1,2-diphenylethylenediamine]-(1,2,3,4-tetramethylbenzene)ruthenium,
[(S,S)-N-methanesulfonyl-1,2-diphenylethylenediamine]-(pentamethylbenzene)ruthenium,
[(R,R)-N-methanesulfonyl-1,2-diphenylethylenediamine](pentamethylbenzene)-ruthenium,
[(S,S)-N-methanesulfonyl-1,2-diphenylethylenediamine]-(hexamethylbenzene)ruthenium,
[(R,R)-N-methanesulfonyl-1,2-diphenylethylenediamine](hexamethylbenzene)ruthenium,
[(S,S)-N-trifluoromethanesulfonyl-1,2-diphenylethylenediamine]benzeneruthenium,
[(R,R)-N-trifluoromethanesulfonyl-1,2-diphenylethylenediamine]benzeneruthenium,
[(S,S)-N-trifluoromethanesulfonyl-1,2-diphenylethylenediamine](p-cymene)ruthenium,
[(R,R)-N-trifluoromethanesulfonyl-1,2-diphenylethylenediamine](p-cymene)ruthenium,
[(S,S)-N-trifluoromethanesulfonyl-1,2-diphenylethylenediamine]-(mesitylene)ruthenium,
[(R,R)-N-trifluoromethanesulfonyl-1,2-diphenylethylenediamine](mesitylene)ruthenium,
[(S,S)-N-trifluoromethanesulfonyl-1,2-diphenylethylenediamine](1,2,4-trimethylbenzene)ruthenium,
[(R,R)-N-trifluoromethanesulfonyl-1,2-diphenylethylenediamine](1,2,4-trimethylbenzene)ruthenium,
[(S,S)-N-trifluoromethane-sulfonyl-1,2-diphenylethylenediamine]-(1,2,4,5-tetramethylbenzene)ruthenium,
[(R,R)-N-trifluoromethane-sulfonyl-1,2-diphenylethylenediamine](1,2,4,5-tetramethyl-benzene)ruthenium,
[(S,S)-N-trifluoromethanesulfonyl-1,2-diphenylethylenediamine](1,2,3,4-tetramethylbenzene)-ruthenium,
[(R,R)-N-trifluoromethanesulfonyl-1,2-diphenylethylenediamine](1,2,3,4-tetramethylbenzene)-ruthenium,
[(S,S)-N-trifluoromethanesulfonyl-1,2-diphenylethylenediamine](pentamethylbenzene)ruthenium,
[(R,R)-N-trifluoromethanesulfonyl-1,2-diphenylethylenediamine](pentamethylbenzene)ruthenium,
[(S,S)-N-trifluoromethanesulfonyl-1,2-diphenylethylenediamine](hexamethylbenzene)ruthenium,
[(R,R)-N-trifluoromethanesulfonyl-1,2-diphenylethylenediamine](hexamethylbenzene)ruthenium,
[(S,S)-N-(2,4,6-triisopropylbenzenesulfonyl)-1,2-diphenylethylenediamine]benzeneruthenium,
[(R,R)-N-(2,4,6-triisopropylbenzenesulfonyl)-1,2-diphenylethylene-diamine]benzeneruthenium,
[(S,S)-N-(2,4,6-triisopropylbenzenesulfonyl)-1,2-diphenylethylenediamine](p-cymene)ruthenium,
[(R,R)-N-(2,4,6-triisopropylbenzene-sulfonyl)-1,2-diphenylethylenediamine](p-cymene)ruthenium,
[(S,S)-N-(2,4,6-triisopropylbenzenesulfonyl)-1,2-diphenylethylenediamine](mesitylene)ruthenium,
[(R,R)-N-(2,4,6-triisopropylbenzenesulfonyl)-1,2-diphenylethylene-diamine](mesitylene)ruthenium,
[(S,S)-N-(2,4,6-triisopropylbenzenesulfonyl)-1,2-diphenylethylenediamine]-(1,2,4-trimethylbenzene)ruthenium,

[(R,R)-N-(2,4,6-triisopropylbenzenesulfonyl)-1,2-diphenyl-ethylenediamine]-(1,2,4-trimethylbenzene)ruthenium,
[(S,S)-N-(2,4,6-triisopropylbenzenesulfonyl)-1,2-diphenyl-ethylenediamine]-(1,2,4,5-tetramethylbenzene)ruthenium,
[(R,R)-N-(2,4,6-triisopropylbenzenesulfonyl)-1,2-diphenyl-ethylenediamine]-(1,2,4,5-tetramethyl-benzene)ruthenium,
[(S,S)-N-(2,4,6-triisopropylbenzenesulfonyl)-1,2-diphenyl-ethylenediamine](1,2,3,4-tetramethylbenzene)-ruthenium,
[(R,R)-N-(2,4,6-triisopropylbenzenesulfonyl)-1,2-diphenyl-ethylenediamine](1,2,3,4-tetramethylbenzene)-ruthenium,
[(S,S)-N-(2,4,6-triisopropylbenzenesulfonyl)-1,2-diphenyl-ethylenediamine](pentamethylbenzene)ruthenium,
[(R,R)-N-(2,4,6-triisopropylbenzenesulfonyl)-1,2-diphenyl-ethylenediamine](pentamethylbenzene)ruthenium,
[(S,S)-N-(2,4,6-triisopropylbenzenesulfonyl)-1,2-diphenyl-ethylenediamine](hexamethylbenzene)ruthenium,
[(R,R)-N-(2,4,6-triisopropylbenzenesulfonyl)-1,2-diphenyl-ethylenediamine](hexamethylbenzene)ruthenium,
[(S,S)-N-(2,4,6-trimethylbenzenesulfonyl)-1,2-diphenylethylenediamine]benzeneruthenium,
[(R,R)-N-(2,4,6-trimethylbenzenesulfonyl)-1,2-diphenyl-ethylene-diamine]benzeneruthenium,
[(S,S)-N-(2,4,6-trimethylbenzene-sulfonyl)-1,2-diphenyl-ethylenediamine](p-cymene)ruthenium,
[(R,R)-N-(2,4,6-trimethylbenzenesulfonyl)-1,2-diphenyl-ethylenediamine](p-cymene)ruthenium,
[(S,S)-N-(2,4,6-trimethylbenzenesulfonyl)-1,2-diphenylethylene-diamine]-(mesitylene)ruthenium,
[(R,R)-N-(2,4,6-trimethylbenzenesulfonyl)-1,2-diphenyl-ethylene-diamine](mesitylene)ruthenium,
[(S,S)-N-(2,4,6-trimethylbenzenesulfonyl)-1,2-diphenylethylenediamine]-(1,2,4-trimethylbenzene)ruthenium,
[(R,R)-N-(2,4,6-trimethylbenzenesulfonyl)-1,2-diphenyl-ethylenediamine]-(1,2,4-trimethylbenzene)ruthenium,
[(S,S)-N-(2,4,6-trimethylbenzenesulfonyl)-1,2-diphenylethylenediamine]-(1,2,4,5-tetramethylbenzene)ruthenium,
[(R,R)-N-(2,4,6-trimethylbenzenesulfonyl)-1,2-diphenyl-ethylenediamine]-(1,2,4,5-tetramethylbenzene)ruthenium,
[(S,S)-N-(2,4,6-trimethylbenzenesulfonyl)-1,2-diphenylethylenediamine](1,2,3,4-tetramethylbenzene)-ruthenium,
[(R,R)-N-(2,4,6-trimethylbenzenesulfonyl)-1,2-diphenyl-ethylenediamine](1,2,3,4-tetramethylbenzene)-ruthenium,
[(S,S)-N-(2,4,6-trimethylbenzenesulfonyl)-1,2-diphenylethylenediamine](pentamethylbenzene)ruthenium,
[(R,R)-N-(2,4,6-trimethylbenzenesulfonyl)-1,2-diphenyl-ethylenediamine](pentamethylbenzene)ruthenium,
[(S,S)-N-(2,4,6-trimethylbenzenesulfonyl)-1,2-diphenylethylenediamine](hexamethylbenzene)ruthenium,
[(R,R)-N-(2,4,6-trimethylbenzenesulfonyl)-1,2-diphenyl-ethylenediamine](hexamethylbenzene)ruthenium,
[(S,S)-N-pentamethylbenzenesulfonyl-1,2-diphenyl-ethylenediamine]benzeneruthenium,
[(R,R)-N-pentamethylbenzenesulfonyl-1,2-diphenylethylene-diamine]benzeneruthenium,
[(S,S)-N-pentamethylbenzene-sulfonyl-1,2-diphenylethylenediamine](cymene)ruthenium,
[(R,R)-N-pentamethylbenzenesulfonyl-1,2-diphenylethylene-diamine](p-cymene)ruthenium,
[(S,S)-N-pentamethylbenzene-sulfonyl-1,2-diphenylethylenediamine]-(mesitylene)ruthenium,
[(R,R)-N-pentamethylbenzenesulfonyl-1,2-diphenylethylene-diamine](mesitylene)ruthenium,
[(S,S)-N-pentamethylbenzene-sulfonyl-1,2-diphenylethylenediamine]-(1,2,4-trimethyl-benzene)ruthenium,
[(R,R)-N-pentamethylbenzenesulfonyl-1,2-diphenylethylene-diamine]-(1,2,4-trimethylbenzene)ruthenium,
[(S,S)-N-pentamethylbenzenesulfonyl-1,2-diphenylethylenediamine]-(1,2,4,5-tetramethylbenzene)ruthenium, [(R,R)-N-pentamethylbenzenesulfonyl-1,2-diphenyl-ethylenediamine]-(1,2,4,5-tetramethylbenzene)ruthenium, [(S,S)-N-pentamethylbenzenesulfonyl-1,2-diphenylethylenediamine](1,2,3,4-tetramethylbenzene)ruthenium, [(R,R)-N-pentamethylbenzenesulfonyl-1,2-diphenylethylene-diamine](1,2,3,4-tetramethylbenzene)-ruthenium, [(S,S)-N-pentamethylbenzenesulfonyl-1,2-diphenylethylene-diamine](pentamethylbenzene)ruthenium,
[(R,R)-N-pentamethylbenzenesulfonyl-1,2-diphenylethyl-ene-diamine](pentamethylbenzene)ruthenium, [(S,S)-N-pentamethylbenzenesulfonyl-1,2-diphenylethylenediamine](hexamethylbenzene)ruthenium,
[(R,R)-N-pentamethylbenzenesulfonyl-1,2-diphenylethylenediamine](hexamethylbenzene)-ruthenium,
[(S,S)-N-(4-tert-butylbenzenesulfonyl)-1,2-diphenylethylenediamine]benzeneruthenium,
[(R,R)-N-(4-tert-butylbenzenesulfonyl)-1,2-diphenylethyl-enediamine]-benzeneruthenium,
[(S,S)-N-(4-tert-butylbenzenesulfonyl)-1,2-diphenylethyl-enediamine](p-cymene)ruthenium,
[(R,R)-N-(4-tert-butylbenzenesulfonyl)-1,2-diphenylethyl-ene-diamine](p-cymene)ruthenium,
[(S,S)-N-(4-tert-butylbenzenesulfonyl)-1,2-diphenylethyl-enediamine]-(mesitylene)ruthenium,
[(R,R)-N-(4-tert-butylbenzene-sulfonyl)-1,2-diphenylethyl-enediamine](mesitylene)ruthenium,
[(S,S)-N-(4-tert-butylbenzenesulfonyl)-1,2-diphenylethyl-enediamine]-(1,2,4-trimethylbenzene)ruthenium,
[(R,R)-N-(4-tert-butylbenzenesulfonyl)-1,2-diphenylethyl-ene-diamine](1,2,4-trimethylbenzene)ruthenium,
[(S,S)-N-(4-tert-butylbenzenesulfonyl)-1,2-diphenylethyl-enediamine](1,2,4,5-tetramethylbenzene)ruthenium,
[(R,R)-N-(4-tert-butylbenzenesulfonyl)-1,2-diphenylethyl-enediamine]-(1,2,4,5-tetramethylbenzene)ruthenium,
[(S,S)-N-(4-tert-butylbenzenesulfonyl)-1,2-diphenylethyl-enediamine](1,2,3,4-tetramethylbenzene)ruthenium,
[(R,R)-N-(4-tert-butylbenzene-sulfonyl)-1,2-diphenylethyl-ene-diamine](1,2,3,4-tetramethylbenzene)ruthenium,
[(S,S)-N-(4-tert-butylbenzene-sulfonyl)-1,2-diphenylethyl-enediamine](pentamethylbenzene)-ruthenium,
[(R,R)-N-(4-tert-butylbenzenesulfonyl)-1,2-diphenylethyl-enediamine](pentamethylbenzene)ruthenium,
[(S,S)-N-(4-tert-butylbenzenesulfonyl)-1,2-diphenylethyl-ene-diamine](hexamethylbenzene)ruthenium,
[(R,R)-N-(4-tert-butylbenzenesulfonyl)-1,2-diphenylethyl-enediamine]-(hexamethylbenzene)ruthenium,
[(S,S)-N-(2-naphthylsulfonyl)-1,2-diphenylethylenediamine]-benzeneruthenium,
[(R,R)-N-(2-naphthylsulfonyl)-1,2-diphenylethylene-diamine]benzeneruthenium,
[(S,S)-N-(2-naphthylsulfonyl)-1,2-diphenylethylenediamine](p-cymene)ruthenium,
[(R,R)-N-(2-naphthylsulfonyl)-1,2-diphenylethylenediamine](p-cymene)ruthenium,
[(S,S)-N-(2-naphthylsulfonyl)-1,2-diphenylethylenediamine]-(mesitylene)ruthenium,
[(R,R)-N-(2-naphthylsulfonyl)-1,2-diphenylethylene-diamine](mesitylene)ruthenium,

[(S,S)-N-(2-naphthylsulfonyl)-1,2-diphenylethylenediamine]-(1,2,4-trimethylbenzene)ruthenium,
[(R,R)-N-(2-naphthylsulfonyl)-1,2-diphenylethylenediamine]-(1,2,4-trimethylbenzene)-ruthenium,
[(S,S)-N-(2-naphthylsulfonyl)-1,2-diphenylethylenediamine]-(1,2,4,5-tetramethylbenzene)-ruthenium,
[(R,R)-N-(2-naphthylsulfonyl)-1,2-diphenyl-ethylenediamine]-(1,2,4,5-tetramethylbenzene)ruthenium,
[(S,S)-N-(2-naphthylsulfonyl)-1,2-diphenylethylene-diamine](1,2,3,4-tetramethylbenzene)-ruthenium,
[(R,R)-N-(2-naphthylsulfonyl)-1,2-diphenylethylenediamine](1,2,3,4-tetramethylbenzene)ruthenium,
[(S,S)-N-(2-naphthyl-sulfonyl)-1,2-diphenylethylenediamine](pentamethylbenzene)-ruthenium,
[(R,R)-N-(2-naphthylsulfonyl)-1,2-diphenylethylenediamine](pentamethylbenzene)ruthenium,
[(S,S)-N-(2-naphthylsulfonyl)-1,2-diphenylethyl-enediamine](hexamethylbenzene)ruthenium,
[(R,R)-N-(2-naphthylsulfonyl)-1,2-diphenylethylenediamine]-(hexamethylbenzene)ruthenium,
[(S,S)-N-(3,5-dimethylbenzenesulfonyl)-1,2-diphenylethylenediamine]benzeneruthenium,
[(R,R)-N-(3,5-dimethylbenzenesulfonyl)-1,2-diphenylethylenediamine]benzeneruthenium,
[(S,S)-N-(3,5-dimethylbenzene-sulfonyl)-1,2-diphenylethylenediamine](p-cymene)ruthenium,
[(R,R)-N-(3,5-dimethylbenzenesulfonyl)-1,2-diphenylethylenediamine](p-cymene)ruthenium,
[(S,S)-N-(3,5-dimethylbenzenesulfonyl)-1,2-diphenylethylenediamine]-(mesitylene)ruthenium,
[(R,R)-N-(3,5-dimethylbenzenesulfonyl)-1,2-diphenylethylene-diamine](mesitylene)ruthenium,
[(S,S)-N-(3,5-dimethylbenzenesulfonyl)-1,2-diphenylethylenediamine]-(1,2,4-trimethylbenzene)ruthenium,
[(R,R)-N-(3,5-dimethylbenzenesulfonyl)-1,2-diphenylethylenediamine]-(1,2,4-trimethylbenzene)ruthenium,
[(S,S)-N-(3,5-dimethylbenzenesulfonyl)-1,2-diphenylethylenediamine]-(1,2,4,5-tetramethylbenzene)ruthenium,
[(R,R)-N-(3,5-dimethylbenzenesulfonyl)-1,2-diphenylethylenediamine]-(1,2,4,5-tetramethylbenzene)ruthenium,
[(S,S)-N-(3,5-dimethylbenzenesulfonyl)-1,2-diphenylethylene-diamine](1,2,3,4-tetramethylbenzene)ruthenium,
[(R,R)-N-(3,5-dimethylbenzenesulfonyl)-1,2-diphenylethylene-diamine](1,2,3,4-tetramethylbenzene)-ruthenium,
[(S,S)-N-(3,5-dimethylbenzenesulfonyl)-1,2-diphenylethylene-diamine](pentamethylbenzene)ruthenium,
[(R,R)-N-(3,5-dimethylbenzenesulfonyl)-1,2-diphenylethylene-diamine](pentamethylbenzene)ruthenium,
[(S,S)-N-(3,5-dimethylbenzenesulfonyl)-1,2-diphenylethylenediamine]-(hexamethylbenzene)ruthenium,
[(R,R)-N-(3,5-dimethylbenzenesulfonyl)-1,2-diphenylethylenediamine]-(hexamethylbenzene)ruthenium, etc.

As specific examples of the ruthenium hydrido complexes represented by the general formula (F), illustrative are
hydrido[(S,S)-N-(p-toluenesulfonyl)-1,2-diphenylethylenediamine]benzeneruthenium,
hydrido[(R,R)-N-(p-toluenesulfonyl)-1,2-diphenylethylenediamine]benzene-ruthenium,
hydrido[(S,S)-N-(p-toluenesulfonyl)-1,2-diphenylethylenediamine](p-cymene)ruthenium,
hydrido[(R,R)-N-(p-toluenesulfonyl)-1,2-diphenylethylenediamine](p-cymene)ruthenium,
hydrido[(S,S)-N-(p-toluenesulfonyl)-1,2-diphenylethylenediamine](mesitylene)ruthenium,
hydrido[(R,R)-N-(p-toluenesulfonyl)-1,2-diphenylethylenediamine](mesitylene)ruthenium,
hydrido[(S,S)-N-(p-toluenesulfonyl)-1,2-diphenylethylenediamine](1,2,4-trimethylbenzene)ruthenium,
hydrido[(R,R)-N-(p-toluene-sulfonyl)-1,2-diphenylethylenediamine](1,2,4-trimethylbenzene)-ruthenium,
hydrido[(S,S)-N-(p-toluenesulfonyl)-1,2-diphenylethylenediamine](1,2,4,5-tetramethylbenzene)ruthenium,
hydrido[(R,R)-N-(p-toluenesulfonyl)-1,2-diphenylethylenediamine](1,2,4,5-tetramethylbenzene)ruthenium,
hydrido[(S,S)-N-(p-toluenesulfonyl)-1,2-diphenylethylenediamine](1,2,3,4-tetramethylbenzene)ruthenium,
hydrido[(R,R)-N-(p-toluenesulfonyl)-1,2-diphenylethylenediamine](1,2,3,4-tetramethylbenzene)ruthenium,
hydrido[(S,S)-N-(p-toluenesulfonyl)-1,2-diphenylethylenediamine]-(pentamethylbenzene)ruthenium,
hydrido[(R,R)-N-(p-toluenesulfonyl)-1,2-diphenylethylenediamine]-(pentamethylbenzene)ruthenium,
hydrido[(S,S)-N-(p-toluenesulfonyl)-1,2-diphenylethylenediamine]-(hexamethylbenzene)ruthenium, hydrido[(R,R)-N-(p-toluenesulfonyl)-1,2-diphenylethylenediamine]-(hexamethylbenzene)ruthenium,
hydrido[(S,S)-N-methane-sulfonyl-1,2-diphenylethylenediamine]benzeneruthenium,
hydrido[(R,R)-N-methanesulfonyl-1,2-diphenylethylene-diamine]benzeneruthenium,
hydrido[(S,S)-N-methanesulfonyl-1,2-diphenylethylenediamine](p-cymene)ruthenium,
hydrido[(R,R)-N-methanesulfonyl-1,2-diphenylethylene-diamine](p-cymene)ruthenium,
hydrido[(S,S)-N-methanesulfonyl-1,2-diphenylethylenediamine]-(mesitylene)ruthenium,
hydrido[(R,R)-N-methanesulfonyl-1,2-diphenylethylenediamine](mesitylene)ruthenium,
hydrido[(S,S)-N-methanesulfonyl-1,2-diphenylethylene-diamine](1,2,4-trimethylbenzene)ruthenium,
hydrido[(R,R)-N-methanesulfonyl-1,2-diphenylethylenediamine](1,2,4-trimethylbenzene)ruthenium,
hydrido[(S,S)-N-methanesulfonyl-1,2-diphenylethylenediamine]-(1,2,4,5-tetramethylbenzene)-ruthenium,
hydrido[(R,R)-N-methanesulfonyl-1,2-diphenylethylenediamine](1,2,4,5-tetramethylbenzene)-ruthenium,
hydrido[(S,S)-N-methanesulfonyl-1,2-diphenylethylenediamine](1,2,3,4-tetramethylbenzene)-ruthenium,
hydrido[(R,R)-N-methanesulfonyl-1,2-diphenylethylenediamine](1,2,3,4-tetramethylbenzene)-ruthenium,
hydrido[(S,S)-N-methanesulfonyl-1,2-diphenylethylenediamine](pentamethylbenzene)ruthenium,
hydrido[(R,R)-N-methanesulfonyl-1,2-diphenylethylenediamine](pentamethylbenzene)-ruthenium,
hydrido[(S,S)-N-methanesulfonyl-1,2-diphenylethylene-diamine](hexamethylbenzene)ruthenium,
hydrido[(R,R)-N-methanesulfonyl-1,2-diphenylethylenediamine]-(hexamethylbenzene)ruthenium,
hydrido[(S,S)-N-trifluoromethanesulfonyl-1,2-diphenylethylenediamine]-benzeneruthenium,
hydrido[(R,R)-N-trifluoromethanesulfonyl-1,2-diphenylethylenediamine]benzeneruthenium,
hydrido[(S,S)-N-trifluoromethanesulfonyl-1,2-diphenylethylenediamine](p-cymene)ruthenium,
hydrido[(R,R)-N-trifluoromethanesulfonyl-1,2-diphenylethylenediamine](p-cymene)ruthenium,
hydrido[(S,S)-N-trifluoromethanesulfonyl-1,2-diphenylethylenediamine](mesitylene)ruthenium,
hydrido-[(R,R)-N-trifluoromethanesulfonyl-1,2-diphenylethylene-diamine](mesitylene)ruthenium,
hydrido[(S,S)-N-trifluoromethanesulfonyl-1,2-diphenylethylenediamine](1,2,4-trimethylbenzene)ruthenium, hydrido[(R,R)-N-trifluoromethanesulfonyl-1,2-diphenyl-ethylenediamine]-(1,2,4-trimethylbenzene)ruthenium,
hydrido[(S,S)-N-trifluoromethanesulfonyl-1,2-diphenylethylenediamine]-(1,2,4,5-tetramethylbenzene)ruthenium,
hydrido[(R,R)-N-trifluoromethane-sulfonyl-1,2-diphenyl-ethylenediamine]-(1,2,4,5-tetramethylbenzene)ruthenium,
hydrido[(S,S)-N-trifluoromethanesulfonyl-1,2-diphenylethylenediamine]-(1,2,3,4-tetramethylbenzene)ruthenium,
hydrido[(R,R)-N-trifluoromethanesulfonyl-1,2-diphenyl-ethylenediamine]-(1,2,3,4-tetramethylbenzene)ruthenium,
hydrido[(S,S)-N-trifluoromethanesulfonyl-1,2-diphenylethylenediamine]-(pentamethylbenzene)ruthenium,
hydrido[(R,R)-N-trifluoromethanesulfonyl-1,2-diphenyl-ethylenediamine]-(pentamethylbenzene)ruthenium,
hydrido[(S,S)-N-trifluoromethanesulfonyl-1,2-diphenylethylenediamine]-(hexamethylbenzene)ruthenium,
hydrido[(R,R)-N-trifluoromethanesulfonyl-1,2-diphenyl-ethylenediamine]-(hexamethylbenzene)ruthenium,
hydrido[(S,S)-N-(2,4,6-triisopropylbenzenesulfonyl)-1,2-diphenylethylene-diamine]benzeneruthenium,
hydrido[(R,R)-N-(2,4,6-triisopropylbenzenesulfonyl)-1,2-diphenylethylene-diamine]benzeneruthenium,
hydrido[(S,S)-N-(2,4,6-triisopropylbenzenesulfonyl)-1,2-diphenylethylenediamine](p-cymene)ruthenium,
hydrido[(R,R)-N-(2,4,6-triisopropylbenzenesulfonyl)-1,2-diphenylethylene-diamine](p-cymene)ruthenium,
hydrido[(S,S)-N-(2,4,6-triisopropylbenzenesulfonyl)-1,2-diphenylethylenediamine]-(mesitylene)ruthenium,
hydrido[(R,R)-N-(2,4,6-triisopropylbenzenesulfonyl)-1,2-diphenylethylene-diamine](mesitylene)ruthenium,
hydrido[(S,S)-N-(2,4,6-triisopropylbenzenesulfonyl)-1,2-diphenylethylenediamine]-(1,2,4-trimethylbenzene)ruthenium,
hydrido[(R,R)-N-(2,4,6-triisopropylbenzenesulfonyl)-1,2-diphenylethylenediamine]-(1,2,4-trimethylbenzene)ruthenium,
hydrido[(S,S)-N-(2,4,6-triisopropylbenzenesulfonyl)-1,2-diphenylethylenediamine]-(1,2,4,5-tetramethylbenzene)ruthenium,
hydrido[(R,R)-N-(2,4,6-triisopropylbenzenesulfonyl)-1,2-diphenylethylene-diamine]-(1,2,4,5-tetramethylbenzene)ruthenium,
hydrido[(S,S)-N-(2,4,6-triisopropylbenzenesulfonyl)-1,2-diphenylethylenediamine](1,2,3,4-tetramethylbenzene)-ruthenium,
hydrido[(R,R)-N-(2,4,6-triisopropylbenzene-sulfonyl)-1,2-diphenylethylenediamine](1,2,3,4-tetramethylbenzene)ruthenium,
hydrido[(S,S)-N-(2,4,6-triisopropylbenzenesulfonyl)-1,2-diphenylethylene-diamine](pentamethylbenzene)ruthenium,
hydrido[(R,R)-N-(2,4,6-triisopropylbenzenesulfonyl)-1,2-diphenylethylene-diamine](pentamethylbenzene)ruthenium,
hydrido[(S,S)-N-(2,4,6-triisopropylbenzenesulfonyl)-1,2-diphenylethylene-diamine](hexamethylbenzene)ruthenium,
hydrido[(R,R)-N-(2,4,6-triisopropylbenzenesulfonyl)-1,2-diphenylethylenediamine](hexamethylbenzene)ruthenium,
hydrido[(S,S)-N-(2,4,6-trimethylbenzenesulfonyl)-1,2-diphenylethylene-diamine]benzeneruthenium,
hydrido[(R,R)-N-(2,4,6-trimethylbenzenesulfonyl)-1,2-diphenylethylene-diamine]benzeneruthenium,
hydrido[(S,S)-N-(2,4,6-trimethylbenzenesulfonyl)-1,2-diphenylethylenediamine](p-cymene)ruthenium,
hydrido[(R,R)-N-(2,4,6-trimethylbenzene-sulfonyl)-1,2-diphenylethylenediamine](p-cymene)ruthenium,
hydrido[(S,S)-N-(2,4,6-trimethylbenzenesulfonyl)-1,2-diphenylethylenediamine](mesitylene)ruthenium,
hydrido-[(R,R)-N-(2,4,6-trimethylbenzenesulfonyl)-1,2-diphenylethylenediamine](mesitylene)ruthenium,
hydrido-[(S,S)-N-(2,4,6-trimethylbenzenesulfonyl)-1,2-diphenylethylenediamine](1,2,4-trimethylbenzene)ruthenium,
hydrido[(R,R)-N-(2,4,6-trimethylbenzenesulfonyl)-1,2-diphenylethylenediamine](1,2,4-trimethylbenzene)ruthenium,
hydrido[(S,S)-N-(2,4,6-trimethylbenzenesulfonyl)-1,2-diphenylethylenediamine](1,2,4,5-tetramethylbenzene)ruthenium,
hydrido[(R,R)-N-(2,4,6-trimethylbenzenesulfonyl)-1,2-diphenylethylenediamine]-(1,2,4,5-tetramethylbenzene)ruthenium,
hydrido[(S,S)-N-(2,4,6-trimethylbenzenesulfonyl)-1,2-diphenylethylene-diamine](1,2,3,4-tetramethylbenzene)ruthenium,
hydrido[(R,R)-N-(2,4,6-trimethylbenzenesulfonyl)-1,2-diphenylethylenediamine](1,2,3,4-tetramethylbenzene)-ruthenium,
hydrido[(S,S)-N-(2,4,6-trimethylbenzenesulfonyl)-1,2-diphenylethylenediamine](pentamethylbenzene)ruthenium,
hydrido[(R,R)-N-(2,4,6-trimethylbenzenesulfonyl)-1,2-diphenylethylenediamine](pentamethylbenzene)ruthenium,
hydrido[(S,S)-N-(2,4,6-trimethylbenzenesulfonyl)-1,2-diphenylethylenediamine](hexamethylbenzene)ruthenium,
hydrido[(R,R)-N-(2,4,6-trimethylbenzenesulfonyl)-1,2-diphenylethylenediamine](hexamethylbenzene)ruthenium,
hydrido[(S,S)-N-pentamethylbenzenesulfonyl-1,2-diphenyl-ethylenediamine]benzeneruthenium,
hydrido[(R,R)-N-pentamethylbenzenesulfonyl-1,2-diphenylethylene-diamine]benzeneruthenium,
hydrido[(S,S)-N-pentamethyl-benzenesulfonyl-1,2-diphenylethylenediamine](p-cymene)ruthenium,
hydrido[(R,R)-N-pentamethylbenzene-sulfonyl-1,2-diphenylethylenediamine](p-cymene)ruthenium,
hydrido[(S,S)-N-pentamethylbenzenesulfonyl-1,2-diphenylethylenediamine](mesitylene)ruthenium,
hydrido[(R,R)-N-pentamethylbenzenesulfonyl-1,2-diphenylethylenediamine](mesitylene)ruthenium,
hydrido-[(S,S)-N-pentamethylbenzenesulfonyl-1,2-diphenylethylene-diamine]-(1,2,4-trimethylbenzene)ruthenium,
hydrido[(R,R)-N-pentamethylbenzenesulfonyl-1,2-diphenylethylenediamine]-(1,2,4-trimethylbenzene)ruthenium,
hydrido[(S,S)-N-pentamethylbenzenesulfonyl-1,2-diphenylethylenediamine]-(1,2,4,5-tetramethylbenzene)ruthenium,
hydrido[(R,R)-N-pentamethylbenzenesulfonyl-1,2-diphenylethylenediamine]-(1,2,4,5-tetramethylbenzene)ruthenium,
hydrido[(S,S)-N-pentamethylbenzenesulfonyl-1,2-diphenylethylenediamine](1,2,3,4-tetramethylbenzene)ruthenium,
hydrido[(R,R)-N-pentamethylbenzenesulfonyl-1,2-diphenylethylene-diamine](1,2,3,4-tetramethylbenzene)ruthenium,
hydrido[(S,S)-N-pentamethylbenzenesulfonyl-1,2-diphenylethylenediamine](pentamethylbenzene)ruthenium, hydrido[(R,R)-N-pentamethylbenzenesulfonyl-1,2-diphenylethylenediamine](pentamethylbenzene)ruthenium,
hydrido[(S,S)-N-pentamethylbenzenesulfonyl-1,2-diphenylethylenediamine](hexamethylbenzene)ruthenium,
hydrido[(R,R)-N-pentamethylbenzenesulfonyl-1,2-diphenylethylenediamine](hexamethylbenzene)ruthenium,
hydrido[(S,S)-N-(4-tert-butylbenzenesulfonyl)-1,2-diphenylethylenediamine]benzeneruthenium,
hydrido[(R,R)-N-(4-tert-butylbenzenesulfonyl)-1,2-diphenylethylene-diamine]benzeneruthenium,
hydrido[(S,S)-N-(4-tert-butylbenzenesulfonyl)-1,2-diphenylethylenediamine](p-cymene)ruthenium,
hydrido[(R,R)-N-(4-tert-butylbenzene-sulfonyl)-1,2-diphenylethylenediamine](p-cymene)ruthenium,
hydrido[(S,S)-N-(4-tert-butylbenzenesulfonyl)-1,2-diphenylethylenediamine](mesitylene)ruthenium,
hydrido[(R,R)-N-(4-tert-butylbenzenesulfonyl)-1,2-diphenylethylenediamine](mesitylene)ruthenium,
hydrido[(S,S)-N-(4-tert-butylbenzenesulfonyl)-1,2-diphenylethylenediamine]-(1,2,4-trimethylbenzene)ruthenium,
hydrido[(R,R)-N-(4-tert-butylbenzenesulfonyl)-1,2-diphenylethylenediamine]-(1,2,4-trimethylbenzene)ruthenium,
hydrido[(S,S)-N-(4-tert-butylbenzenesulfonyl)-1,2-diphenyl-ethylenediamine]-(1,2,4,5-tetramethylbenzene)-ruthenium,
hydrido[(R,R)-N-(4-tert-butylbenzenesulfonyl)-1,2-diphenyl-ethylenediamine]-(1,2,4,5-tetramethylbenzene)ruthenium,
hydrido[(S,S)-N-(4-tert-butylbenzenesulfonyl)-1,2-diphenylethylenediamine](1,2,3,4-tetramethylbenzene)-ruthenium,
hydrido[(R,R)-N-(4-tert-butylbenzenesulfonyl)-1,2-diphenylethylenediamine](1,2,3,4-tetramethylbenzene)-ruthenium,
hydrido[(S,S)-N-(4-tert-butylbenzenesulfonyl)-1,2-diphenylethylenediamine](pentamethylbenzene)ruthenium,
hydrido[(R,R)-N-(4-tert-butylbenzenesulfonyl)-1,2-diphenylethylenediamine](pentamethylbenzene)ruthenium,
hydrido[(S,S)-N-(4-tert-butylbenzenesulfonyl)-1,2-diphenylethylenediamine](hexamethylbenzene)ruthenium,
hydrido[(R,R)-N-(4-tert-butylbenzenesulfonyl)-1,2-diphenylethylenediamine](hexamethylbenzene)ruthenium,
hydrido[(S,S)-N-(2-naphthylsulfonyl)-1,2-diphenylethylene-diamine]benzeneruthenium,
hydrido[(R,R)-N-(2-naphthyl-sulfonyl)-1,2-diphenylethylenediamine]benzeneruthenium,
hydrido[(S,S)-N-(2-naphthylsulfonyl)-1,2-diphenylethylene-diamine](p-cymene)ruthenium,
hydrido[(R,R)-N-(2-naphthyl-sulfonyl)-1,2-diphenylethylenediamine](p-cymene)ruthenium,
hydrido[(S,S)-N-(2-naphthylsulfonyl)-1,2-diphenylethylene-diamine](mesitylene)ruthenium,
hydrido[(R,R)-N-(2-naphthylsulfonyl)-1,2-diphenylethylenediamine](mesitylene)ruthenium,
hydrido[(S,S)-N-(2-naphthylsulfonyl)-1,2-diphenylethylenediamine]-(1,2,4-trimethylbenzene)ruthenium,
hydrido[(R,R)-N-(2-naphthylsulfonyl)-1,2-diphenylethylene-diamine](1,2,4-trimethylbenzene)ruthenium,
hydrido[(S,S)-N-(2-naphthylsulfonyl)-1,2-diphenylethylenediamine](1,2,4,5-tetramethylbenzene)ruthenium,
hydrido[(R,R)-N-(2-naphthylsulfonyl)-1,2-diphenyl-ethylenediamine](1,2,4,5-tetramethylbenzene)ruthenium,
hydrido[(S,S)-N-(2-naphthylsulfonyl)-1,2-diphenylethylene-diamine](1,2,3,4-tetramethylbenzene)ruthenium,
hydrido-[(R,R)-N-(2-naphthylsulfonyl)-1,2-diphenylethylene-diamine](1,2,3,4-tetramethylbenzene)ruthenium,
hydrido-[(S,S)-N-(2-naphthylsulfonyl)-1,2-diphenylethylenediamine]-(pentamethylbenzene)ruthenium,
hydrido[(R,R)-N-(2-naphthylsulfonyl)-1,2-diphenylethylenediamine](pentamethyl-benzene)ruthenium,
hydrido[(S,S)-N-(2-naphthylsulfonyl)-1,2-diphenylethylenediamine](hexamethylbenzene)ruthenium,
hydrido[(R,R)-N-(2-naphthylsulfonyl)-1,2-diphenylethylened-iamine](hexamethylbenzene)ruthenium,
hydrido[(S,S)-N-(3,5-dimethylbenzenesulfonyl)-1,2-diphenylethylenediamine]-benzeneruthenium,
hydrido[(R,R)-N-(3,5-dimethylbenzene-sulfonyl)-1,2-diphenylethylenediamine]benzeneruthenium,
hydrido[(S,S)-N-(3,5-dimethylbenzenesulfonyl)-1,2-diphenylethylenediamine](p-cymene)ruthenium,
hydrido[(R,R)-N-(3,5-dimethylbenzenesulfonyl)-1,2-diphenylethylene-diamine](p-cymene)ruthenium,
hydrido[(S,S)-N-(3,5-dimethylbenzenesulfonyl)-1,2-diphenylethylenediamine]-(mesitylene)ruthenium,
hydrido[(R,R)-N-(3,5-dimethylbenzenesulfonyl)-1,2-diphenylethylene-diamine](mesitylene)ruthenium,
hydrido[(S,S)-N-(3,5-dimethylbenzenesulfonyl)-1,2-diphenylethylenediamine]-(1,2,4-trimethylbenzene)ruthenium,
hydrido[(R,R)-N-(3,5-dimethylbenzenesulfonyl)-1,2-diphenylethylenediamine]-(1,2,4-trimethylbenzene)ruthenium,
hydrido[(S,S)-N-(3,5-dimethylbenzenesulfonyl)-1,2-diphenylethylenediamine](1,2,4,5-tetramethylbenzene)-ruthenium,
hydrido[(R,R)-N-(3,5-dimethylbenzenesulfonyl)-1,2-diphenylethylenediamine](1,2,4,5-tetramethylbenzene)-ruthenium,
hydrido[(S,S)-N-(3,5-dimethylbenzenesulfonyl)-1,2-diphenylethylenediamine](1,2,3,4-tetramethylbenzene)-ruthenium,
hydrido[(R,R)-N-(3,5-dimethylbenzenesulfonyl)-1,2-diphenylethylenediamine](1,2,3,4-tetramethylbenzene)-ruthenium,
hydrido[(S,S)-N-(3,5-dimethylbenzenesulfonyl)-1,2-diphenylethylenediamine](pentamethylbenzene)ruthenium,
hydrido[(R,R)-N-(3,5-dimethylbenzenesulfonyl)-1,2-diphenylethylenediamine](pentamethylbenzene)ruthenium,
hydrido[(S,S)-N-(3,5-dimethylbenzenesulfonyl)-1,2-diphenylethylenediamine](hexamethylbenzene)ruthenium,
hydrido[(R,R)-N-(3,5-dimethylbenzenesulfonyl)-1,2-diphenylethylenediamine](hexamethylbenzene)ruthenium, etc.

In order to obtain optically active nitro compounds and cyano compounds in a higher yield and a higher optical purity, among these it is preferable to use
[(S,S)-N-(2,4,6-triisopropylbenzenesulfonyl)-1,2-diphenylethylenediamine](hexamethylbenzene)ruthenium,
[(R,R)-N-(2,4,6-triisopropylbenzenesulfonyl)-1,2-diphenylethylenediamine](hexamethylbenzene)ruthenium,
[(S,S)-N-(4-tert-butylbenzenesulfonyl)-1,2-diphenylethylenediamine](hexamethylbenzene)ruthenium,
[(R,R)-N-(4-tert-butylbenzenesulfonyl)-1,2-diphenylethylenediamine](hexamethylbenzene)ruthenium, [(S,S)-N-pentamethylbenzenesulfonyl-1,2-diphenylethylenediamine](hexamethylbenzene)ruthenium,
[(R,R)-N-pentamethylbenzenesulfonyl-1,2-diphenylethylenediamine](hexamethylbenzene)ruthenium,
[(S,S)-N-(2,4,6-trimethylbenzenesulfonyl)-1,2-diphenylethylenediamine](hexamethylbenzene)ruthenium,
[(R,R)-N-(2,4,6-trimethylbenzenesulfonyl)-1,2-diphenylethylenediamine](hexamethylbenzene)ruthenium,
[(S,S)-N-(3,5-dimethylbenzenesulfonyl)-1,2-diphenylethylenediamine](hexamethylbenzene)ruthenium,
[(R,R)-N-(3,5-dimethylbenzenesulfonyl)-1,2-diphenylethylenediamine](hexamethylbenzene)ruthenium,
[(S,S)-N-(p-toluenesulfonyl)-1,2-diphenylethylenediamine]-(hexamethylbenzene)ruthenium,
[(R,R)-N-(p-toluenesulfonyl)-1,2-diphenylethylenediamine](hexamethylbenzene)ruthenium,
[(S,S)-N-methanesulfonyl-1,2-diphenylethylenediamine]-(hexamethylbenzene)ruthenium,

[(R,R)-N-methanesulfonyl-1,2-diphenylethylenediamine](hexamethylbenzene)ruthenium,

[(S,S)-N-(p-toluenesulfonyl)-1,2-diphenylethylenediamine]-(p-cymene)ruthenium,

[(R,R)-N-(p-toluenesulfonyl)-1,2-diphenylethylenediamine](p-cymene)ruthenium.

In the embodiment of the invention, the optically active nitrogen-containing compound, the periodic table group VIII metal compound and the compounds (A) and (B) can be reacted under mixing. More preferably, the asymmetric metal complex is beforehand prepared using the optically active nitrogen-containing compound and the periodic table group VIII metal compound, and then the compounds (A) and (B) are mixed to react under the presence of this asymmetric metal complex. If the preparation of this asymmetric metal complex is carried out in the presence of a hydrogen-donating compound, an asymmetric metal hydrido complex is obtained, and in the absence of the hydrogen-donating compound an asymmetric metal amido complex is obtained. As catalysts in the asymmetric reactions, either of an asymmetric metal amido and asymmetric hydrido complexes can be used. The preparation method of asymmetric metal complexes are described in Angew. Chem., Int. Ed. Engl. 1997, 36, 285-288 or J. Org. Chem. 1999, 64, 2186-2187. Further, an asymmetric metal complex is prepared by reaction of the asymmetric metal hydrido complex or asymmetric metal amido complex, which are prepared from the optically active nitrogen-containing compound and the periodic table group VIII metal compound, with the compound (B), and then this as a catalyst can be reacted mixing with the compounds (A) and (B).

Reactions can be carried out in various solvents. For example, an aliphatic hydrocarbon such as pentane, hexane, cyclopentane or cyclohexane, an aromatic compound such as benzene, toluene or xylene, a halogen compound such as dichloromethane, a ketone type solvent such as acetone, methyl ethyl ketone or cyclohexanone, an alcohol type solvent such as methanol, ethanol, 2-propanol, 2-methyl-2-propanol or 2-methyl-2-butanol, and an organic compound such as tetrahydrofuran, diethyl ether, dimethyl sulfoxide (DMSO), dimethylformamido (DMF), acetonitrile or ethyl acetate, can be used alone or together.

A reaction temperature can be about −50° C. to 100° C. considering economy. More practically, the reaction can be carried out at −30° C. to 40° C. Although a reaction time is different according to the reaction conditions such as a reaction-substrate concentration, temperature and pressure, the reaction ends during few minutes to 100 hours. Purification of a product can be carried out by a known method such as chromatography, distillation or recrystallization.

EXAMPLES

In the following the invention is explained in more detail showing the examples, however, the invention is not limited by the following examples. Further, % ee in the examples represents enantiomer excess, and S/C represents molar ratio of a substrate against a catalyst (molar ratio of the substrate against ruthenium).

Example 1

Preparation of methyl(R)-2-methoxycarbonyl-4-nitro-3-phenylbutanoate

[(S,S)-N-(2,4,6-triisopropylbenzenesulfonyl)-1,2-diphenylethylenediamine](hexamethylbenzene)ruthenium (14.8 mg, 0.02 mmol, S/C=50), trans-β-nitrostyrene (149 mg, 1.0 mmol), dimethyl malonate (114 µl, 1.0 mmol) and toluene (1 ml) were added into Schlenk (20 ml) under an argon atmosphere, and stirred at 30° C. for 24 hours. $^1$HNMR determination of the solution showed that the yield of the product was 94%. The reaction solution was purified by flash column chromatography (hexane/acetone=80/20, SiO$_2$), and the optical purity was measured by HPLC (CHIRALPACK AD manufactured by Daicel Co., Ltd., hexane:2-propanol=90:10, flow rate 0.5 ml/min, detection by 210 nm), resulting to 87% ee.

Examples 2-7

Except changing catalysts at S/C=50 against trans-β-nitrostyrene (149 mg, 1.0 mmol) as follows, the reactions were carried out in the same condition as that of the example 1.

TABLE 1

| | Catalyst | Yield (%) | Optical Purity (%) |
|---|---|---|---|
| Example 2 | [(S,S)-N-(4-tert-butylbenzenesulfonyl)-1,2-diphenylethylenediamine](hexamethylbenzene)ruthenium | 55 | 85 |
| Example 3 | [(S,S)-N-pentamethylbenzenesulfonyl-1,2-diphenylethylenediamine](hexamethylbenzene)ruthenium | 88 | 90 |
| Example 4 | [(S,S)-N-(2,4,6-trimethylbenzenesulfonyl)-1,2-diphenylethylenediamine](hexamethylbenzene)ruthenium | 81 | 81 |
| Example 5 | [(S,S)-N-(3,5-dimethylbenzenesulfonyl)-1,2-diphenylethylenediamine](hexamethylbenzene)ruthenium | 53 | 79 |
| Example 6 | [(S,S)-N-(p-toluenesulfonyl)-1,2-diphenylethylenediamine]-(hexamethylbenzene)ruthenium | 60 | 78 |
| Example 7 | [(S,S)-N-methanesulfonyl-1,2-diphenylethylenediamine]-(hexamethylbenzene)ruthenium | 45 | 77 |

Example 8

Preparation of methyl(R)-2-methoxycarbonyl-4-nitro-3-phenylbutanoate

[(S,S)-N-(2,4,6-triisopropylbenzenesulfonyl)-1,2-diphenylethylenediamine](hexamethylbenzene)ruthenium (14.8 mg, 0.02 mmol, S/C=50), trans-β-nitrostyrene (149 mg, 1.0 mmol), dimethyl malonate (114 µl, 1.0 mmol) and toluene (1 ml) were added into Schlenk (20 ml) under an argon atmosphere, and stirred at 0° C. for 60 hours. $^1$HNMR determination of the solution showed that the yield of the product was 99%. The reaction solution was purified by flash column chromatography (hexane/acetone=80/20, SiO$_2$), and the optical purity was measured by HPLC (CHIRALPACK AD manufactured by Daicel Co., Ltd., hexane:2-propanol=90:10, flow rate 0.5 ml/min, detection by 210 nm), resulting to 91% ee.

Example 9

Preparation of methyl(R)-2-methoxycarbonyl-4-nitro-3-phenylbutanoate

[(S,S)-N-(pentamethylbenzenesulfonyl)-1,2-diphenylethylenediamine](hexamethylbenzene)ruthenium (13.7 mg, 0.02 mmol, S/C=50), trans-β-nitrostyrene (149 mg, 1.0 mmol), dimethyl malonate (114 µl, 1.0 mmol) and toluene (1 ml) were added into Schlenk (20 ml) under an argon atmosphere, and stirred at −20° C. for 48 hours. The reaction solution was purified by flash column chromatography (hexane/acetone=80/20, SiO$_2$), showing that the yield of the product was 93%. The optical purity was measured by HPLC (CHIRALPACK AD manufactured by Daicel Co., Ltd., hexane:2-propanol=90:10, flow rate 0.5 ml/min, detection by 210 mn), resulting to 94% ee.

Example 10

Preparation of ethyl(R)-2-ethoxycarbonyl-4-nitro-3-phenylbutanoate

[(S,S)-N-(pentamethylbenzenesulfonyl)-1,2-diphenylethylenediamine](hexamethylbenzene)ruthenium (13.7 mg, 0.02 mmol, S/C=50), trans-β-nitrostyrene (149 mg, 1.0 mmol), diethyl malonate (152 μl, 1.0 mmol) and toluene (1 ml) were added into Schlenk (20 ml) under an argon atmosphere, and stirred at −20° C. for 48 hours. The reaction solution was purified by flash column chromatography (hexane/acetone=80/20, $SiO_2$), showing that the yield of the product was 89%. The optical purity was measured by HPLC (CHIRALPACK AD manufactured by Daicel Co., Ltd., hexane:2-propanol=95:5, flow rate 0.5 ml/min, detection by 210 nm), resulting to 93% ee.

Example 11

Preparation of methyl 3-(4-chlorophenyl)-2-methoxycarbonyl-4-nitrobutanoate

[(S,S)-N-(4-tert-butylbenzenesulfonyl)-1,2-diphenylethylenediamine](hexamethylbenzene)ruthenium (12.9 mg, 0.02 mmol, S/C=50), 4-chloro-62-nitrostyrene (184 mg, 1.0 mmol), dimethyl malonate (114 μl, 1.0 mmol) and toluene (1 ml) were added into Schlenk (20 ml) under an argon atmosphere, and stirred at 30° C. for 24 hours. The reaction solution was purified by flash column chromatography (hexane/acetone=80/20, $SiO_2$), showing that the yield of the product was 42%. The optical purity was measured by HPLC (CHIRALPACK AD manufactured by Daicel Co., Ltd., hexane:2-propanol=90:10, flow rate 0.5 ml/min, detection by 210 nm), resulting to 79% ee.

Example 12

Preparation of methyl 2-methoxycarbonyl-3-(4-methylphenyl)-4-nitrobutanoate

[(S,S)-N-(4-tert-butylbenzenesulfonyl)-1,2-diphenylethylenediamine](hexamethylbenzene)ruthenium (12.9 mg, 0.02 mmol, S/C=50), 4-methyl-β-nitrostyrene (184 mg, 1.0 mmol), dimethyl malonate (114 μl, 1.0 mmol) and toluene (1 ml) were added into Schlenk (20 ml) under an argon atmosphere, and stirred at 30° C. for 24 hours. $^1$HNMR determination of the solution showed that the yield of the product was 51%. The reaction solution was purified by flash column chromatography (hexane/acetone=80/20, $SiO_2$), and the optical purity was measured by HPLC (CHIRALPACK AD manufactured by Daicel Co., Ltd., hexane:2-propanol=90:10, flow rate 0.5 ml/min, detection by 210 nm), resulting to 82% ee.

Example 13

Preparation of methyl 4-cyano-2-methoxycarbonyl-3-phenylbutanoate

[(S,S)-N-trifluoromethanesulfonyl-1,2-diphenylethylenediamine](hexamethylbenzene)ruthenium (6.1 mg, 0.01 mmol, S/C=50), cinnamonitrile (65 μl, 0.5 mmol), dimethylmalonate (57 μl, 0.5 mmol) and toluene (0.5 ml) were added into Schlenk (20 ml) under an argon atmosphere, and stirred at 30° C. for 48 hours. $^1$HNMR determination of the solution showed that the yield of the product was 45%. The reaction solution was purified by flash column chromatography (hexane/acetone=90/10, $SiO_2$), and the optical purity was measured by HPLC (CHIRALPACK AS manufactured by Daicel Co., Ltd, hexane:2-propanol=85:15, flow rate 1.0 ml/min, detection by 210 nm), resulting to 60% ee.

Examples 14-16

Except changing catalysts at S/C=50 against cinnamonitrile (65 μl, 0.5 mmol) to [(S,S)-N-methanesulfonyl-1,2-diphenylethylenediamine](hexamethylbenzene)ruthenium, [(S,S)-N-(p-toluenesulfonyl)-1,2-diphenylethylenediamine](hexamethylbenzene)ruthenium and [(S,S)-N-methanesulfonyl-1,2-diphenylethylenediamine](p-cymene)ruthenium, the reactions were carried out in the same condition as that of the example 13. As the results, methyl 4-cyano-2-methoxycarbonyl-3-phenylbutanoate could be prepared.

Example 17

Preparation of ethyl 4-cyano-2-ethoxycarbonyl-3-phenylbutanoate

[(S,S)-N-methanesulfonyl-1,2-diphenylethylenediamine]-(hexamethylbenzene)ruthenium (5.5 mg, 0.01 mmol, S/C=50), cinnamonitrile (65 μl, 0.5 mmol), diethyl malonate (76 μl, 0.5 mmol) and toluene (0.5 ml) were added into Schlenk (20 ml) under an argon atmosphere, and stirred at 30° C. for 48 hours. $^1$HNMR determination of the solution showed that the yield of the product was 46%. The reaction solution was purified by flash column chromatography (hexane/acetone=90/10, $SiO_2$), and the optical purity was measured by HPLC (CHIRALPACK AS manufactured by Daicel Co., Ltd., hexane:2-propanol=90:10, flow rate 0.5 ml/min, detection by 210 nm), resulting to 56% ee.

Example 18

Preparation of methyl 2-methoxycarbonyl-3-(4-methylphenyl)-4-nitrobutanoate

[(S,S)-N-(pentamethylbenzenesulfonyl)-1,2-diphenylethylenediamine](hexamethylbenzene)ruthenium (13.7 mg, 0.02 mmol, S/C=50), 4-methyl-β-nitrostyrene (1.0 mmol), dimethyl malonate (114 μl, 1.0 mmol) and toluene (1 ml) were added into Schlenk (20 ml) under an argon atmosphere, and stirred at −20° C. for 48 hours. The reaction solution was purified by flash column chromatography (hexane/acetone=80/20, $SiO_2$), showing that the isolation yield of the product was 71%. The optical purity was measured by HPLC (CHIRALPACK AD manufactured by Daicel Co., Ltd., hexane:2-propanol=90:10, flow rate 0.5 ml/min, detection by 210 nm), resulting to 92% ee.

Example 19

Preparation of methyl 3-(4-fluorophenyl)-2-methoxycarbonyl-4-nitrobutanoate

Except for changing 4-methyl-β-nitrostyrene to 4-fluoro-β-nitrostyrene, the reaction temperature to 30° C. and the reaction time to 24 hours, the reaction was carried out in the same condition as that of the example 18. As the result, the product was obtained in the isolation yield 60% and the optical purity 86% ee.

Example 20

Preparation of methyl 2-methoxycarbonyl-3-[(3,4-methylenedioxy)phenyl]-4-nitrobutanoate

[(S,S)-N-(pentamethylbenzenesulfonyl)-1,2-diphenylethylenediamine](hexamethylbenzene)ruthenium (13.7 mg, 0.02 mmol, S/C=50), 5-[(1E)-2-nitroethenyl]-1,3-benzodioxole (193 mg, 1.0 mmol), dimethyl malonate (137 µl, 1.2 mmol) and toluene (4 ml) were added into Schlenk (20 ml) under an argon atmosphere, and stirred at 0° C. for 48 hours. The reaction solution was purified by flash column chromatography (hexane/acetone=90/10, $SiO_2$), showing that the isolation yield of the product was 99%. The optical purity was measured by HPLC (CHIRALPACK AS-H manufactured by Daicel Co., Ltd., hexane:2-propanol=90:10, flow rate 1 m/min, detection by 210 nm), resulting to 95% ee.

Example 21

Preparation of methyl 3-(2,6-dimethoxyoxyphenyl)-2-methoxycarbonyl-4-nitrobutanoate

[(S,S)-N-(pentamethylbenzenesulfonyl)-1,2-diphenylethylenediamine](hexamethylbenzene)ruthenium (13.7 mg, 0.02 mmol, S/C=50), 1,3-dimethoxy-2-[(1E)-2-nitroethenyl]-benzene (209 mg, 1.0 mmol), dimethylmalonate (137 µl, 1.2 mmol) and toluene (2 ml) were added into Schlenk (20 ml) under an argon atmosphere, and stirred at 0° C. for 72 hours. The reaction solution was purified by flash column chromatography (hexane/acetone=90/10, $SiO_2$), showing that the isolation yield of the product was 81%. The optical purity was measured by HPLC (CHIRALPACK AD manufactured by Daicel Co., Ltd., hexane:2-propanol=95:5, flow rate 0.5 ml/min, detection by 210 nm), resulting to 90% ee.

Example 22

Preparation of methyl 2-methoxycarbonyl-4-nitro 3-(2-thienyl)-butanoate

[(S,S)-N-(pentamethylbenzenesulfonyl)-1,2-diphenylethylenediamine](hexamethylbenzene)ruthenium (13.7 mg, 0.02 mmol, S/C=50), 2-[(1E)-2-nitroethenyl]-thiophene (155 mg, 1.0 mmol), dimethyl malonate (137 µl, 1.2 mmol) and toluene (1 ml) were added into Schlenk (20 ml) under an argon atmosphere, and stirred at −20° C. for 48 hours. The reaction solution was purified by flash column chromatography (hexane/acetone=90/10, $SiO_2$), showing that the isolation yield of the product was 91%. The optical purity was measured by HPLC (CHIRALPACK AD manufactured by Daicel Co., Ltd., hexane:2-propanol=90:10, flow rate 0.5 m/min, detection by 210 mn), resulting to 97% ee.

Example 23

Preparation of methyl 3-(2-furyl)-2-methoxycarbonyl-4-nitrobutanoate

Except for changing 2-[(1E)-2-nitroethenyl]-thiophene to 2-[(1E)-2-nitroethenyl]-furane, the reaction was carried out in the same condition as that of the example 22. As the result, the product was obtained in the isolation yield 91% and the optical purity 98% ee. Further, the optical purity was measured by HPLC (CHIRALCEL OD-H manufactured by Daicel Co., Ltd., hexane:2-propanol=90:10, flow rate 0.5 ml/min, detection by 210 nm).

Example 24

Preparation of methyl 3-(4-chlorophenyl)-2-methoxycarbonyl-4-nitrobutanoate

[(S,S)-N-(pentamethylbenzenesulfonyl)-1,2-diphenylethylenediamine](hexamethylbenzene)ruthenium (13.7 mg, 0.02 mmol, S/C=50), 4-chloro-β-nitrostyrene (1.0 mmol), dimethyl malonate (114 µl, 1.0 mmol) and toluene (1 ml) were added into Schlenk (20 ml) under an argon atmosphere, and stirred at −20° C. for 48 hours. The reaction solution was purified by flash column chromatography (hexane/acetone=80/20, $SiO_2$), showing that the isolation yield of the product was 24%. The optical purity was measured by HPLC (CHIRALPACK AD manufactured by Daicel Co., Ltd., hexane:2-propanol=90:10, flow rate 0.5 ml/min, detection by 210 nm), resulting to 95% ee.

Example 25

Preparation of methyl 3-(4-fluorophenyl)-2-methoxycarbonyl-4-nitrobutanoate

Except for changing 4-chloro-β-nitrostyrene to 4-fluoro-β-nitrostyrene, the reaction was carried out in the same condition as that of the example 24. As the result, the product was obtained in the isolation yield 83% and the optical purity 93% ee.

Example 26

Preparation of methyl 3-(3-cyclopenthoxy-4-methoxyphenyl)2-methoxycarbonyl-4-nitrobutanoate Except for changing 4-chloro-β-nitrostyrene to 3-cyclopenthoxy-4-methoxy-β-nitrostyrene, and toluene from 1 ml to 2 ml, the reaction was carried out in the same condition as that of the example 24. As the result, the product was obtained in the isolation yield 95%, and the optical purity was measured by HPLC (CHIRALCEL OJ-H manufactured by Daicel Co., Ltd., hexane:2-propanol=90:10, flow rate 1.0 ml/min, detection by 210 nm), resulting to 95% ee.

Example 27

Preparation of methyl 2-methoxycarbonyl-2-methyl-4-nitro-3-phenylbutanoate

[(S,S)-N-(pentamethylbenzenesulfonyl)-1,2-diphenylethylenediamine](hexamethylbenzene)ruthenium (13.7 mg, 0.02 mmol, S/C=50), trans-β-nitrostyrene (149 mg, 1.0 mmol), dimethyl methylmalonate (160 µl, 1.2 mmol) and toluene (1 ml) were added into Schlenk (20 ml) under an argon atmosphere, and stirred at −20° C. for 48 hours. The reaction solution was purified by flash column chromatography (hexane/acetone=90/10, $SiO_2$), showing that the isolation yield of the product was 94%. The optical purity was measured by HPLC (CHIRALPACK AD manufactured by Daicel Co., Ltd., hexane:2-propanol=95:5, flow rate 0.5 m/min, detection by 210 nm), resulting to 97% ee.

Example 28

Preparation of methyl 2-acetyl-4-nitro-3-phenylbutanoate

Except for changing dimethyl methylmalonate to methyl acetoacetate, the reactions was carried out in the same condition as that of the example 27. As the result, the product was obtained in the isolation yield 95%. Decarboxylation was carried out heating the product in aqueous hydrochloric acid, and its optical purity was measured by HPLC (CHIRALCEL OJ-H manufactured by Daicel Co., Ltd., hexane:2-propanol=95:5, flow rate 1.0 ml/min, detection by 210 nm), resulting to 58% ee.

Example 29

Preparation of methyl 4-methyl-2-(2-nitro-1-phenylethyl)-3-oxopentanoate

Except for changing dimethyl methylmalonate to methyl isobutyrylacetate, the reaction was carried out in the same condition as that of the example 27. As the result, the product was obtained in the isolation yield 97%. Decarboxylation was carried out heating the product in aqueous hydrochloric acid under stirring, and its optical purity was measured by HPLC (CHIRALCEL OJ-H manufactured by Daicel Co., Ltd., hexane:2-propanol=95:5, flow rate 1.0 ml/min, detection by 210 nm), resulting to 94% ee.

Example 30

Preparation of methyl 2-(2-nitro-1-phenylethyl)-3-oxopentanoate

Except for changing dimethyl methylmalonate to methyl propionylacetate, the reaction was carried out in the same condition as that of the example 27. As the result, the product was obtained in the isolation yield 97%. Decarboxylation was carried out heating the product in aqueous hydrochloric acid under stirring, and its optical purity was measured by HPLC (CHIRALCEL OJ-H manufactured by Daicel Co., Ltd., hexane:2-propanol=90:10, flow rate 1.0 ml/min, detection by 210 nm), resulting to 89% ee.

Example 31

Preparation of methyl 2-bezoyl-4-nitro-3-phenylbutanoate

Except for changing dimethyl methylmalonate to ethyl benzoylacetate, the reaction was carried out in the same condition as that of the example 28. As the result, the product was obtained in the isolation yield 96%. The optical purity was measured by HPLC (CHIRALPAK AD manufactured by Daicel Co., Ltd., hexane:2-propanol=95:5, flow rate 1.0 ml/min, detection by 210 nm), resulting to 93% ee.

Example 32

Preparation of 3-methylcarbonyl-1-nitro-2-phenyl-4-pentanone

Except for changing dimethyl methylmalonate to acetylacetone, the reaction was carried out in the same condition as that of the example 27. As the result, the product was obtained in the isolation yield 90%.

All the examples are summarized in Table-2.

TABLE 2

| Example | General formula(A) | General formula (B) | Asymmetric metal complex | Reaction temperature (° C.) | Reaction time | Yield (%) | Optical purity (%) |
|---|---|---|---|---|---|---|---|
| 1 | trans-β-nitrostyrene | dimethyl malonate | [(S,S)-N-(2,4,6-triisopropylbenzenesulfonyl)-1,2-diphenylethylenediamine-](hexamethylbenzene)ruthenium | 30 | 24 | 94 | 87 |
| 2 | trans-β-nitrostyrene | dimethyl malonate | [(S,S)-N-(4-tert-butylbenzenesulfonyl)-1,2-diphenylethylenediamine](hexamethylbenzene)ruthenium | 30 | 24 | 55 | 85 |
| 3 | trans-β-nitrostyrene | dimethyl malonate | [(S,S)-N-pentamethylbenzenesulfonyl-1,2-diphenylethylenediamine](hexamethylbenzene)ruthenium | 30 | 24 | 88 | 90 |
| 4 | trans-β-nitrostyrene | dimethyl malonate | [(S,S)-N-(2,4,6-trimethylbenzenesulfonyl)-1,2-diphenylethylenediamine](hexamethylbenzene)ruthenium | 30 | 24 | 81 | 81 |
| 5 | trans-β-nitrostyrene | dimethyl malonate | [(S,S)-N-(3,5-dimethylbenzenesulfonyl)-1,2-diphenylethylenediamine](hexamethylbenzene)ruthenium | 30 | 24 | 53 | 79 |
| 6 | trans-β-nitrostyrene | dimethyl malonate | [(S,S)-N-(p-toluenesulfonyl)-1,2-diphenylethylenediamine]-(hexamethylbenzene)ruthenium | 30 | 24 | 60 | 78 |
| 7 | trans-β-nitrostyrene | dimethyl malonate | [(S,S)-N-methanesulfonyl-1,2-diphenylethylenediamine]-(hexamethylbenzene)ruthenium | 30 | 24 | 45 | 77 |
| 8 | trans-β-nitrostyrene | dimethyl malonate | [(S,S)-N-(2,4,6-triisopropylbenzenesulfonyl)-1,2-diphenylethylenediamine-](hexamethylbenzene)ruthenium | 0 | 60 | 99 | 91 |
| 9 | trans-β-nitrostyrene | dimethyl malonate | [(S,S)-N-(pentamethylbenzenesulfonyl)-1,2-diphenylethylenediamine](hexamethylbenzene)ruthenium | −20 | 48 | 93 | 94 |
| 10 | trans-β-nitrostyrene | diethyl malonate | [(S,S)-N-(pentamethylbenzenesulfonyl)-1,2-diphenylethylenediamine](hexamethylbenzene)ruthenium | −20 | 48 | 89 | 93 |
| 11 | 4-chloro-β-nitrostyrene | dimethyl malonate | [(S,S)-N-(4-tert-butylbenzenesulfonyl)-1,2-diphenylethylenediamine](hexamethylbenzene)ruthenium | 30 | 24 | 42 | 79 |
| 12 | 4-methyl-β-nitrostyrene | dimethyl malonate | [(S,S)-N-(4-tert-butylbenzenesulfonyl)-1,2-diphenylethylenediamine](hexamethylbenzene)ruthenium | 30 | 24 | 51 | 82 |
| 13 | cinnamonitrile | dimethyl malonate | [(S,S)-N-trifluoromethanesulfonyl-1,2-diphenylethylenediamine](hexamethylbenzene)ruthenium | 30 | 48 | 45 | 60 |
| 14 | cinnamonitrile | dimethyl malonate | [(S,S)-N-methanesulfonyl-1,2-diphenylethylenediamine](hexamethylbenzene)ruthenium | 30 | 48 | — | — |
| 15 | cinnamonitrile | dimethyl malonate | [(S,S)-N-(p-toluenesulfonyl)-1,2-diphenylethylenediamine](hexamethylbenzene)ruthenium | 30 | 48 | — | — |
| 16 | cinnamonitrile | dimethyl malonate | [(S,S)-N-methanesulfonyl-1,2-diphenylethylenediamine](p-cymene)ruthenium | 30 | 48 | — | — |
| 17 | cinnamonitrile | diethyl malonate | [(S,S)-N-methanesulfonyl-1,2-diphenylethylenediamine]-(hexamethylbenzene)ruthenium | 30 | 48 | 46 | 56 |

TABLE 2-continued

| Example | General formula(A) | General formula (B) | Asymmetric metal complex | Reaction temperature (° C.) | Reaction time (%) | Yield (%) | Optical purity (%) |
|---|---|---|---|---|---|---|---|
| 18 | 4-methyl-β-nitrostyrene | dimethyl malonate | [(S,S)-N-(pentamethylbenzenesulfonyl)-1,2-diphenylethylenediamine] (hexamethylbenzene)ruthenium | −20 | 48 | 71 | 92 |
| 19 | 4-fluoro-β-nitrostyrene | dimethyl malonate | [(S,S)-N-(pentamethylbenzenesulfonyl)-1,2-diphenylethylenediamine] (hexamethylbenzene)ruthenium | 30 | 24 | 60 | 86 |
| 20 | 5-[(1E)-2-nitro-ethenyl]-1,3-benzodioxole | dimethyl malonate | [(S,S)-N-(pentamethylbenzenesulfonyl)-1,2-diphenylethylenediamine] (hexamethylbenzene)ruthenium | 0 | 48 | 99 | 95 |
| 21 | 1,3-dimethoxy-2-[(1E)-2-nitro-ethenyl]-benzene | dimethyl malonate | [(S,S)-N-(pentamethylbenzenesulfonyl)-1,2-diphenylethylenediamine] (hexamethylbenzene)ruthenium | 0 | 72 | 81 | 90 |
| 22 | 2-[(1E)-2-nitro-ethenyl]-thiophene | dimethyl malonate | [(S,S)-N-(pentamethylbenzenesulfonyl)-1,2-diphenylethylenediamine] (hexamethylbenzene)ruthenium | −20 | 48 | 91 | 97 |
| 23 | 2-[(1E)-2-nitro-ethenyl]-furane | dimethyl malonate | [(S,S)-N-(pentamethylbenzenesulfonyl)-1,2-diphenylethylenediamine] (hexamethylbenzene)ruthenium | −20 | 48 | 91 | 98 |
| 24 | 4-chloro-β-nitrostyrene | dimethyl malonate | [(S,S)-N-(pentamethylbenzenesulfonyl)-1,2-diphenylethylenediamine] (hexamethylbenzene)ruthenium | −20 | 48 | 24 | 95 |
| 25 | 4-fluoro-β-nitrostyrene | dimethyl malonate | [(S,S)-N-(pentamethylbenzenesulfonyl)-1,2-diphenylethylenediamine] (hexamethylbenzene)ruthenium | −20 | 48 | 83 | 93 |
| 26 | 3-cyclopenthoxy-4-methoxy-β-nitrostyrene | dimethyl malonate | [(S,S)-N-(pentamethylbenzenesulfonyl)-1,2-diphenylethylenediamine] (hexamethylbenzene)ruthenium | −20 | 48 | 95 | 95 |
| 27 | trans-β-nitrostyrene | Dimethyl methylmalonate | [(S,S)-N-(pentamethylbenzenesulfonyl)-1,2-diphenylethylenediamine] (hexamethylbenzene)ruthenium | −20 | 48 | 94 | 97 |
| 28 | trans-β-nitrostyrene | methyl acetoacetate | [(S,S)-N-(pentamethylbenzenesulfonyl)-1,2-diphenylethylenediamine] (hexamethylbenzene)ruthenium | −20 | 48 | 95 | 58 |
| 29 | trans-β-nitrostyrene | methyl isobutyryl-acetate | [(S,S)-N-(pentamethylbenzenesulfonyl)-1,2-diphenylethylenediamine] (hexamethylbenzene)ruthenium | −20 | 48 | 97 | 94 |
| 30 | trans-β-nitrostyrene | methyl propionyl-acetate | [(S,S)-N-(pentamethylbenzenesulfonyl)-1,2-diphenylethylenediamine] (hexamethylbenzene)ruthenium | −20 | 48 | 97 | 89 |
| 31 | trans-β-nitrostyrene | ethyl benzoyl-acetate | [(S,S)-N-(pentamethylbenzenesulfonyl)-1,2-diphenylethylenediamine] (hexamethylbenzene)ruthenium | −20 | 48 | 96 | 93 |
| 32 | trans-β-nitrostyrene | acetyl-acetone | [(S,S)-N-(pentamethylbenzenesulfonyl)-1,2-diphenylethylenediamine] (hexamethylbenzene)ruthenium | −20 | 48 | 90 | — |

In some embodiments, the optically active nitro compounds and cyano compounds that can be obtained by the process of the invention can be utilized as intermediates for the synthesis of drugs, etc.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A process for preparing an optically active compound, comprising reacting a compound represented by the general formula (A)

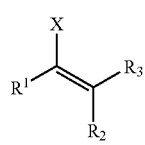

(A)

wherein $R^1$ is an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s), or is a hydrogen atom, a halogen atom, a carboxyl, ester, amido, hydroxyl, alkoxy or amino group; $R^2$ and $R^3$ are each independently a hydrogen atom, an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s); X is a nitro or cyano group; wherein $R^1$ and $R^2$, $R^1$ and $R^3$ or $R^2$ and $R^3$ can form a ring binding each other; and a compound represented by the general formula (B)

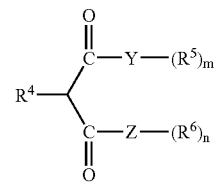

(B)

wherein $R^4$ is a hydrogen atom, a halogen atom, an amido, amino, alkoxy, nitro or cyano group, an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s); $R^5$ and $R^6$ are each independently a hydrogen atom, an aromatic monocyclic or aromatic polycyclic hydrocarbon group which can have (a) substituent(s), a saturated or unsaturated aliphatic or alicyclic hydrocarbon group which can have (a) substituent(s), or a straight or branched alkoxyl groups of carbon number 1 to 20; wherein $R^4$ and $R^5$, $R^4$ and $R^6$, or $R^5$ and $R^6$ can form a ring binding each other; Y and Z are independently a single bond, an oxygen, sulfur, nitrogen or phosphorus atom; and m and n are each other independently 1 or 2 wherein in the case that Y and Z are a single bond, an oxygen or sulfur atom, m and n are 1, and wherein in the case that Y and Z are a nitrogen or phosphorus atom, m and n are 2 with an asymmetric metal complex obtained by the action of an optically active nitrogen-containing compound represented by the general formula (D)

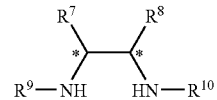

(D)

wherein $R^7$ and $R^8$ are each independently an aromatic monocyclic or aromatic polycyclic hydrocarbon group which can have (a) substituent(s), a saturated or unsaturated aliphatic or alicyclic hydrocarbon group which can have (a) substituent(s), a hetero-monocyclic or hetero-polycyclic group which can have (a) substituent(s), wherein $R^7$ and $R^8$ can form a ring binding each other; $R^9$ and $R^{10}$ are each independently a hydrogen atom, an alkyl, acyl, carbamoyl, thioacyl, thiocarbamoyl, alkylsulfonyl or arylsulfonyl group; and wherein * represents an asymmetric carbon atom; and a periodic table group VIII metal complex, to produce optically active compounds represented by the general formula (C)

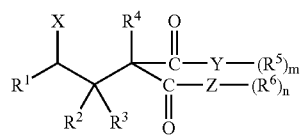
(C)

wherein $R^1$, $R^2$, $R^3$, $R^4$, $R^5$, $R^6$, X, Y, Z, m and n have the same meaning as described above.

2. The process for preparing an optically active compound according to claim 1, wherein Y and Z in above compound (B) are both oxygen atoms.

3. The process for preparing an optically active compound according to claim 1, wherein Y in above compound (B) is an oxygen atom and Z is a single bond, or Y is a single bond and Z is an oxygen atom.

4. The process for preparing an optically active compound according to claim 1, wherein in the optically active nitrogen-containing compound represented by the general formula (D), $R^{10}$ is represented by the structure

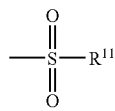

wherein $R^{11}$ is an alkyl or aryl group which can have (a) substituent(s).

5. The process for preparing an optically active compound according to claim 1, wherein in the optically active nitrogen-containing compound represented by the general formula (D), $R^7$ is represented by the structure,

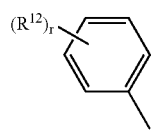

$R^8$ is represented by the structure,

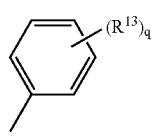

and $R^{10}$ is represented by the structure

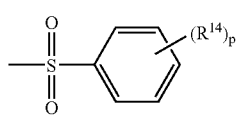

wherein $R^{12}$, $R^{13}$ and $R^{14}$ are each independently a hydrogen atom, an alkyl group, a halogen atom or an alkoxyl group and wherein p, q and r are each independently an integer of 1 to 5.

6. The process for preparing an optically active compound according to any one of claims 1-3, 4 and 5, wherein the periodic table group VIII metal complex is a ruthenium compound.

7. The process for preparing an optically active compound according to claim 1, wherein the asymmetric metal complex is an asymmetric ruthenium amido complex represented by the general structure (E)

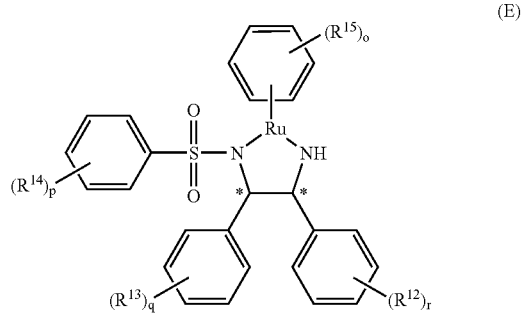
(E)

wherein $R^{12}$, $R^{13}$, $R^{14}$ are each independently a hydrogen atom, an alkyl group, a halogen atom or an alkoxyl group; wherein p, q and r are each independently an integer of 1 to 5; wherein $R^{15}$ is a methyl, ethyl, propyl, isopropyl or tert-butyl group; wherein o is an integer of 0 to 6 and wherein * represents an asymmetric carbon atom.

8. The process for preparing an optically active compound according to claim 1, wherein the asymmetric metal complex is a asymmetric ruthenium hydrido complex represented by the general structure (F)

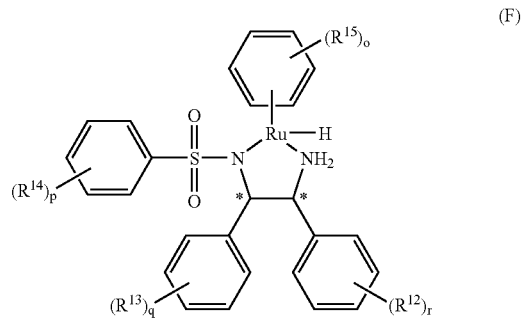
(F)

wherein $R^{12}$, $R^{13}$, $R^{14}$, are each independently a hydrogen atom, an alkyl group, a halogen atom or an alkoxyl group; wherein p, q and r are each independently an integer of 1 to 5 wherein $R^{15}$ is a methyl, ethyl, propyl, isopropyl or tert-butyl group; wherein o is an integer of 0 to 6, and wherein * represents an asymmetric carbon atom.

* * * * *

UNITED STATES PATENT AND TRADEMARK OFFICE
CERTIFICATE OF CORRECTION

PATENT NO. : 7,332,622 B2  Page 1 of 1
APPLICATION NO. : 10/934338
DATED : February 19, 2008
INVENTOR(S) : Masahito Watanabe et al.

It is certified that error appears in the above-identified patent and that said Letters Patent is hereby corrected as shown below:

On the title page, item (73), should read:

Kanto Kagaku Kabushiki Kaisha,
Chuo-ku Tokyo (JP)

Signed and Sealed this

Eighteenth Day of August, 2009

David J. Kappos
*Director of the United States Patent and Trademark Office*